US008690750B2

(12) United States Patent
Krueger

(10) Patent No.: US 8,690,750 B2
(45) Date of Patent: Apr. 8, 2014

(54) SYSTEM AND METHOD FOR MEASURING AND MINIMIZING THE EFFECTS OF VERTIGO, MOTION SICKNESS, MOTION INTOLERANCE, AND/OR SPATIAL DISORIENTATION

(75) Inventor: Wesley W O Krueger, San Antonio, TX (US)

(73) Assignee: Wesley W. O. Krueger, San Antonio, TX (US)

( * ) Notice: Subject to any disclaimer, the term of this patent is extended or adjusted under 35 U.S.C. 154(b) by 204 days.

(21) Appl. No.: 13/108,683

(22) Filed: May 16, 2011

(65) Prior Publication Data

US 2011/0282130 A1 Nov. 17, 2011

Related U.S. Application Data

(60) Provisional application No. 61/345,040, filed on May 14, 2010.

(51) Int. Cl.
*A61M 21/00* (2006.01)
(52) U.S. Cl.
USPC .......................................................... 600/27
(58) Field of Classification Search
USPC ................ 600/27, 26; 701/1, 4, 8, 9; 340/967
See application file for complete search history.

(56) References Cited

U.S. PATENT DOCUMENTS

| | | | |
|---|---|---|---|
| 3,157,853 A * | 11/1964 | Hirsch | 340/965 |
| 5,051,735 A | 9/1991 | Furukawa | |
| 5,067,941 A | 11/1991 | Hendricks | |
| 5,599,274 A * | 2/1997 | Widjaja et al. | 600/27 |
| 5,614,897 A * | 3/1997 | Durnford | 340/973 |
| 5,629,848 A | 5/1997 | Repperger | |
| 5,790,085 A | 8/1998 | Hergesheimer | |
| 5,966,680 A | 10/1999 | Butnaru | |
| 6,099,124 A | 8/2000 | Hidaji | |
| 6,228,021 B1 | 5/2001 | Kania | |
| 6,320,579 B1 * | 11/2001 | Snyder et al. | 345/419 |
| 6,361,508 B1 | 3/2002 | Johnson et al. | |
| 6,443,913 B1 | 9/2002 | Kania | |
| 6,497,649 B2 | 12/2002 | Parker et al. | |
| 6,568,396 B1 | 5/2003 | Anthony | |
| 6,896,655 B2 * | 5/2005 | Patton et al. | 600/300 |
| 6,924,428 B1 | 8/2005 | Payne et al. | |
| 6,932,090 B1 | 8/2005 | Reschke et al. | |
| 7,128,705 B2 | 10/2006 | Brendley et al. | |
| 7,266,446 B1 | 9/2007 | Pelosi | |
| 7,474,335 B2 | 1/2009 | Basson et al. | |
| 7,488,294 B2 | 2/2009 | Torch | |
| 7,490,611 B2 | 2/2009 | Bromwich | |
| 7,643,394 B2 | 1/2010 | Kashihara et al. | |
| 7,667,700 B1 | 2/2010 | Neely, III et al. | |

(Continued)

OTHER PUBLICATIONS

C.A. Hughes, L. Proctor, "Benign Paroxysmal Positional Vertigo," The Laryngoscope, 107: 607-613 (1997).*

(Continued)

*Primary Examiner* — Jacqueline Cheng
*Assistant Examiner* — Eileen Foley
(74) *Attorney, Agent, or Firm* — Kilpatrick Townsend & Stockton LLP

(57) ABSTRACT

An improved System and Method to provide a human user with symbology to ameliorate, prevent or shorten the duration of disorientation or motion sickness effects caused by spatial disorientation.

20 Claims, 14 Drawing Sheets

(56) References Cited

U.S. PATENT DOCUMENTS

| | | | |
|---|---|---|---|
| 7,717,841 B2 | 5/2010 | Brendley et al. | |
| 7,722,526 B2 | 5/2010 | Kim | |
| 7,893,935 B1 | 2/2011 | Neely, III et al. | |
| 7,925,391 B2 | 4/2011 | Sanders-Reed | |
| 8,063,798 B2 | 11/2011 | Cernasov et al. | |
| 8,218,006 B2 | 7/2012 | De Mers et al. | |
| 2004/0024287 A1* | 2/2004 | Patton et al. | 600/27 |
| 2006/0252979 A1* | 11/2006 | Vesely et al. | 600/27 |
| 2009/0295602 A1* | 12/2009 | Cernasov et al. | 340/974 |

OTHER PUBLICATIONS

T. Brandt, R.B. Daroff, "The Multisensory Physiological and Pathological Vertigo Syndromes," Ann Neurol 7:195-203 (1980).*

R. Davies, L. Luxon, D. Bamiou, S. Shorvon, "Chapter 14: Neuro-Otology: Problems of Dizziness, Balance and Hearing," Neurology: A Queen Square Textbook, edited by Charles Clarke, Robin Howard, Martin Rossor, and Simon Shorvon, Blackwell Publishing Ltd. (2009).*

* cited by examiner

SYSTEM AND METHOD FOR MEASURING AND MINIMIZING THE EFFECTS OF VERTIGO, MOTION SICKNESS, MOTION INTOLERANCE, AND/OR SPATIAL DISORIENTATION

RELATED APPLICATION(S)

This application claims priority of Provisional Application Ser. No. 61/345,040 filed on 14 May 2010.

TECHNICAL FIELD OF THE INVENTION

The present invention generally relates to systems and methods for avoiding problems associated with compromise or human performance or loss of control due to vertigo, motion sickness and spatial disorientation.

BACKGROUND OF THE INVENTION

Motion sickness, spatial disorientation and vertigo have been acknowledged as a wide-spread problem, affecting a significant portion of world population to varying degrees. Researchers report that up to 60% of the population have some motion intolerance. It has been reported that motion sickness affects nearly one third of all people who travel by land, sea, or air. Individuals are affected daily by motion sickness and spatial disorientation while riding in automobiles, trains, buses, planes or other transport. The Greeks provided the first written historical account of motion sickness. The Roman Cicero claimed he would rather be killed in battle than suffer the tortures of nausea maxis. Motion sickness has even been used as a form of punishment. One of the world's most famous mariners, Admiral Lord Nelson reportedly never adapted to motion sickness. Napolean's General Carbuccia refused to use camels for Napoleon's army, because of the issues with motion (2) Even Lawrence of Arabia is reported to have experienced Camel sickness.

It is also known that some people are more susceptible than others; for example, women are more sensitive to motion than men by a ratio of about 5:3. Some are more susceptible due to physical reasons such as age. Studies show a significant genetic contribution to a propensity to motion sickness. It has been well observed that poor ventilation, bad odors, smoking, eating large fatty meals and alcohol can make motion sickness more pronounced. Susceptibility to motion sickness begins at about age two, and for most will peak in adolescence and decline gradually. However, many adults remain highly sensitive caused by any motion, particularly when combined with either an absence of a visual reference or to significant levels of visual stimuli. In fact, a provocative visual stimulus has been shown to be the most influential cause of motion sickness symptoms. Reading in a moving vehicle, abruptly moving the head (such as looking down) while a vehicle is moving can provoke symptoms. Fear, anxiety and other psychological factors can contribute to the onset of motion sickness. Some people can get sick just thinking about an upcoming trip or flight.

For those who experience the symptoms, the result is often disabling, with nausea, vomiting, sweating, and unsteadiness, while feeling cold, clammy and disorientated. In addition, the term "sopite syndrome" was coined to refer to the apathy, passivity, and lack of concentration characteristic of motion sickness.

The occurrence of motion sickness can approach 100% in cruise ship passengers on rough seas. Seasickness, a common form of motion sickness, is frequent among naval personnel, where 60% to 90% percent of inexperienced sailors can suffer from seasickness. Experienced crew-members are not immune. Up to 60% of experienced crew-members have been affected in these conditions. This becomes a major problem in modern seamanship in which small crews are responsible for the operation of sensitive and sophisticated equipment. During the invasion of Normandy, in World War II, the seas were reportedly very high causing the landing crafts to pitch and yaw, like a kite in a windstorm. The soldiers were lying and sitting in flat bottomed crafts and were using huge buckets for vomiting and urinating, which soon overflowed after boarding. As thousands of men were lying in the vomit, urine and rain they debarked in a state of terror, which was compounded by their symptoms of seasickness, and attempted to perform at a high level in order to survive in combat. Many of these soldiers had to overcome the most debilitating effects of motion sickness to survive. Volumes of data documents motion sickness's severe effect on human performance of even basic tasks.

Spatial disorientation along with motion sickness are significant problems in aviation. In motion provocative environments, spatial disorientation and motion sickness cause not only a loss in human performance (affecting cognitive and motor skills), but a loss of expensive aircraft and human life. Thousands of deaths have been attributed to aviation accidents caused by being spatially disoriented. A recent study has shown that almost Ninety to One Hundred percent (90-100%) of aircrew have reported at least one incidence of spatial disorientation (SD) during their flying careers. SD accounted for Eleven to Fourteen percent (11-14%) of USAF mishaps and a mishap fatality rate of 69%, with risk of SD significantly increased in helicopters and fighter/attack aircraft and at night. The most frequent experienced SD episodes are "leans" (Ninety-Two percent (92%)), loss of horizon due to atmospheric conditions (Eighty-Two percent (82%)), misleading altitude cues (Seventy-Nine percent 79%)), sloping horizon (Seventy-Five percent (75%)), and SD arising from distraction (Sixty-Six percent (66%)). In a review of aviation mishaps from 1987-1997 there was an average of one fatal SD accident every Eleven (11) days in the United States. The death of John F. Kennedy Jr. was an example of a spatial disorientation accident and unknown to many were thirty other reported crashes that same day, with at least one other due to spatial disorientation. According to FAA statistics, SD and loss of situational awareness causes Fifteen to Seventeen percent (15%-17%) of fatal general aviation crashes annually. More significantly, Nine (9) out of ten (10) SD mishaps result in a fatality. The Air Force Safety Center FY93-02 mishap analysis reported that Class A mishaps resulted in Two Hundred Forty-Three (243) destroyed aircraft, Three Hundred Ten (310) fatalities, and an economic loss of Six Billion Two Hundred Thirty Million dollars ($6.23 billion). Airsickness has also been identified as a flight training issue. A motion sickness history questionnaire obtained from student pilots in the Air Force revealed an incidence of airsickness of fifty percent (50%). In a questionnaire to B-1 and B-52 bomber crewmembers, it was reported to be a frequent occurrence among non-pilots in both aircraft, and experienced crew-members were more likely to report an impact on their duties.

Space motion sickness is experienced by Sixty to Eighty percent (60%-80%) of astronauts during the first Two to Three (2-3) days in microgravity and by a similar proportion during their first few days after return to Earth. Up to Ninety percent (90%) of astronauts experience spatial disorientation during reentry and landing of the shuttle, with prevalence proportional to the length of the mission. Exposure to microgravity rearranges the relationships among signals from visual, skin, joint, muscle, and vestibular receptors. Congruence between vestibular signals and those from other receptors, as well as between the vestibular otolith and semicircular canal receptors, is disrupted by the absence of gravity. This lack of congruence between sensory exposure to provocative real or apparent motion leads to the progressive cardinal symptoms of terrestrial motion sickness. Space motion sickness may vary slightly with flushing more common than pallor, stomach awareness, malaise, loss of appetite, and sudden vomiting, often without prodromal nausea.

Simulator sickness is another example of motion sickness, and many military pilots have reported at least one symptom following simulator exposure. In a study of Coast Guard aviators undergoing flight simulator testing, Sixty-Four percent (64%) reported adverse symptoms during the first simulator flight and Thirty-Nine percent (39%) did so during the last flight. Thirty-Six percent (36%) of pilots reported motion sickness when training on a Blackhawk flight simulator.

More recently, simulator sickness in virtual environments (VE) has become an important issue. Virtual reality is already a popular technology for entertainment purposes, and both the U.S. Army and Navy are interested in the training applications of virtual environments. However, some users of VE experience discomfort during, and sometimes after, a session in a simulated environment, in equivalent fashion to simulator sickness already noted for flight and driving simulators.

There have been many theories about the cause of motion sickness, spatial disorientation and vertigo. The earlier Gut Theory proposed that vomiting was a reflex response to irritation of the gastric mucosa possibly caused by movements of the viscera which caused abdominal contractions and overstimulated the Pacinian corpuscles or overproduction of bile in the liver. There are also Vascular or Blood Theories: those that proposed a lack of blood flow to the brain (cerebral anemia) and those that proposed too much blood going to the brain (cerebral hyperemia). These conditions were theorized to be caused by numerous mechanisms. One such theory suggested that vascular deficiency was due to the irritation of the eyes by perceived motion, which, by reflex action, produced spasm in the cerebral capillaries causing giddiness and vomiting. Other vascular theories argued that motion produced cerebral hyperemia, which destabilized brain cells in the vomiting center of the medulla oblongata.

Other theories attributed it to respiratory factors, shock to the central and autonomic nervous system, or due to infections. The vestibular and other sensory contributions came later, and were built upon some of the early work of Purkinje, Flourens, and Meniere.

Over-stimulation of the semicircular canals theory evolved in the 1990s. This lost favor when it became clear that motion in the absence of vestibular stimulation could be as provocative as the primary sensory organs.

A fluid shift theory with assumptions of active or passive shifts in the body fluids to the central nervous system and vestibulo-auditory mechanisms was considered a cause in space flight.

The neural mismatch theory suggested the problems to be in the central integrative mechanism, which is involved in interpreting the significance of the sensory environment. It was proposed that the conflict between visual or vestibular input systems or between separate components of the vestibular system is of secondary importance to mismatch occurring between ongoing sensory experience and long-term memory. The limbic system was suspected as perhaps being the neural mismatch center of the brain.

Currently, the sensory conflict theory appears to be the dominant theory favored by researchers in that the majority of investigators agree that it is not solely the movement or movement stimulus that results in motion sickness, but rather a conflict in movement information detected by the different sensory modalities of the inner ear, vision, and proprioception. A conflict of visual and vestibular (inner ear) information, as it relates to postural control and visual stabilization, is certainly a critical factor. Investigators now also agree that it is primarily an incongruence of visual and vestibular sensory information regarding movement and orientation that results in motion sickness. Incongruence between the semicircular canals and the otolithic organ input has also been implicated as the provocative stimulus in seasickness and in the onset of motion sickness associated with weightlessness. Another contributing factor which may trigger susceptibility to motion sickness may be the mass size differences of the utricular otoconia between the left and right sides in some people, as seen in fish.

Within the sensory conflict concept has arisen an 'incongruence in the visual system' theory which can be called a Velocity Storage Theory. The vestibular nerve communicates head velocity and estimates of angular displacements require further central nervous system processing (i.e. integration). There is some inconsistency between velocity-based ocular studies and displacement-based perceptual studies. Most oculographic studies of vestibular function are based on measurements of the slow phase velocity of the eye. If a monkey or man is rotated at constant velocity in the dark, the velocity of the slow phase of the nystagmus decays exponentially with a time constant of Fifteen to Twenty seconds (15-20 sec). Direct recordings of the vestibular nerve in monkeys have shown the head velocity signal, transmitted by the vestibular nerve, has a time constant of decay of only Seven to Ten (7-10 sec). The duration of the eye velocity curve (i.e. a nystagmus response) is therefore longer, outlasting the sensation or perception curve. The perception of angular velocity is based on signals subserved by the brainstem velocity storage system. Thus the head velocity signal appears to be stored in the brain and then released onto ocular motor neurons for the generation of nystagmus. Brainstem circuits in the vicinity of the vestibular nuclei, behaving as mathematical integrators, are thought to mediate this storage process. There is evidence that motion sickness is generated through this velocity storage and can be reduced by reducing the angular vestibular ocular reflex time constant. Others support a multi-factor explanation of motion sickness, involving both sensory conflict and eye movement.

Vestibular Dysfunction. Postural control requires a complex interaction of visual and proprioceptive sensory inputs providing external orientation reference frames while the internal reference frame is provided by the vestibular system. An estimated Twenty percent (20%) of the general population is affected by a vestibular disorder. Ninety million (9 million) Americans (Forty-Two percent (42%) of the population) will complain of dizziness at least once during lifetime, and, of these, Eight percent (80%) will have a vestibular component. There are more than Ten million (10 million) physician visits annually for dizziness or balance complaints (National Balance Centers/Vestibular Disorders Association), with a cost of greater than one billion dollars per year. Persistent vestibular dysfunction can occur following a variety of insults to the vestibular system, including infections, ototoxicity, trauma, chronic ear pathology, tumors, Meniere's disease, surgery and other idiopathic causes. Acoustic tumor surgery and vestibular nerve section, performed for disabling vertigo in patients with Meniere's disease, usually result in rapid compensation. However some patients, particularly non-Meniere's disease patients, have a prolonged period of unsteadiness without compensation for a long period of time. The resulting disability can be devastating. It has also been shown that postural instability precedes motion sickness with provocative visual stimuli. All these vestibular impairments cause disequilibrium, blurred vision, disorientation, and vertigo, which in turn cause dysfunction in many activities of daily living and in social interactions that traditional medical treatments may not address.

Mismatches can be caused where there is a mismatch between stimuli as processed by the brain. Mismatches can occur where there is motion, or where there is no motion. These mismatches may be caused by delays in the delivery or processing of the stimuli or mismatch of stimuli even without delay. Examples of mismatches are seen in persons suffering from vertigo or persons in a virtual space such as a video game or flight simulator or targeting system.

Butnaru in U.S. Pat. No. 5,966,680 taught the use of a device and method which operates as an artificial labyrinth to eliminate sensory mismatch between a person's natural labyrinth vestibular system and the vision system of the user. The device provided the user with an alternative means for determining true orientation within his environment through a system of visual cues. However Butnaru system of cues have been determined to have some limitations and the Butnaru system is lacking in its integration with user environments, which may cause sensory mismatches.

There is a need for improvements to systems which avoid vertigo, motion sickness, and spatial disorientation integrated in motion sensory provocative environments to avoid problems associated with compromised human performance or even loss of user control.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Preferred embodiments of the present invention are illustrated in the FIGUREs, like numerals being used to refer to like and corresponding parts of the various drawings.

The present invention generally relates to systems and methods for avoiding problems associated with loss of control due to vertigo, motion sickness and spatial disorientation. More specifically, the present invention relates to improvements to cue symbology provided in Butnaru in U.S. Pat. No. 5,966,680, and integration of the device into particular user environments.

Figure 1:
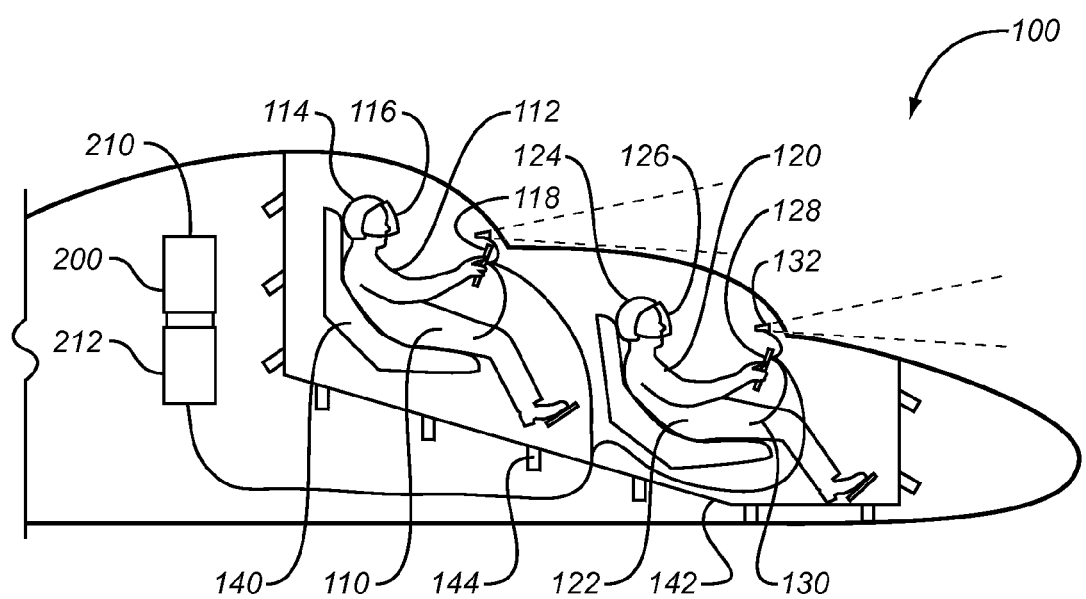
FIG. 1 illustrates an example of an environment that is provocative to motion sickness and spatial disorientation.

FIG. 1 illustrates an exemplar environment 100 that is highly provocative to motion sickness and spatial disorientation: an aircraft. In the example shown there are two crew-members 110 and 120. Each crew-member is equipped with a flight suit 112 and 122, helmets 114 and 124 which may include a helmet mounted display or eyewear display 116 and 126. The crew-members are also equipped with various sensors 130, 132 which monitor various biometric parameters and environmental data. By way of example sensors may include: blood oxygen, pressure, heart rate and other EKG waveform information, respiration rate and gas levels delivered and exhaled. Position of the user's head and trunk (core body); core temperature and skin temperature; limb movement muscle flex/contraction and relaxation; eye movement; EKG parameters; cabin pressure and oxygen and other gas levels; vibration, light levels; aircraft acceleration, speed and position.

These sensors are typically directly or indirectly input into the electronics or avionics 200. The electronics may include central processors system(s) 210 and subsystems 212 and sensor interfaces (not shown separately). Each crew-member also typically has a console 118, 128 which provides the user with the mean to interface with the avionics and electronics to access information and to give instructions. In the illustration the crew members are seated in seats 140 which may be set with rockets or charges for emergency ejection from the aircraft 100. In the illustration shown, both crew members are in a cockpit structure 142 which is fitted with rockets or explosive charges 144 to eject the cockpit as a capsule.

Figure 2:
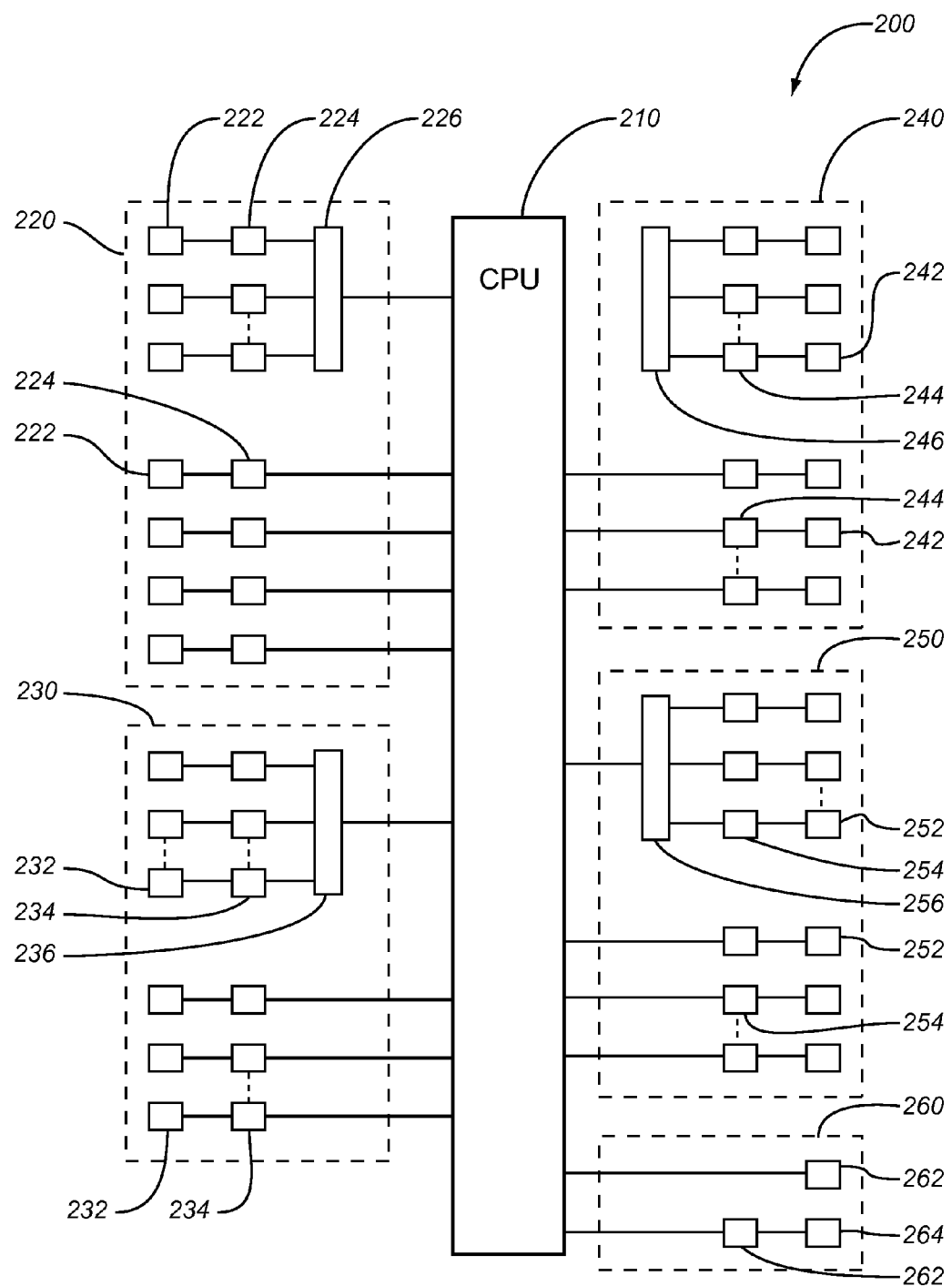
FIG. 2 illustrates an example of major avionics hardware components.

FIG. 2 is an illustration of an example electronics/avionics 200 hardware components. At the center is shown a central processing unit CPU 210 typically a special purpose computer. For the purposes of this illustration the avionics subsystems have been divided into five different types. On the left side are shown the vehicle centric hardware subsystems and on the left side are shown the human centric subsystems. The vehicle centric subsystems have been divided into two groups: the vehicle centric inputs 220 and the vehicle centric outputs 230. On the right side they have been divided into three groups the human centric inputs—passive 240, the human centric inputs active 250, and the human centric outputs 260. The following lists are not intended to be exhaustive but merely to serve as examples.

The vehicle centric inputs may include sensors 222 which may be connected to the CPU 210 via a sensor interface 224 with or without a preprocessor 246. These vehicle centric inputs 220 generally fall into three major categories: control, performance, and navigation. The following are by way of example types of aircraft centric inputs: AHRS (attitude heading reference system) and AAHRS (altitude, attitude, heading reference system) systems which may include instrument settings actuals, which may further include multiple measures. For example altitude may include sea level, hard deck and/or density altitude. Attitude may include pitch bank and yaw; and the heading may be magnetic and/or true. Speed measure may also be captured which may include ground speed, indicated air speed, calibrated and/or true and may include a mach value. Navigational aids may include HSI (Horizontal Situation Indicator, HSI with CDI (course deviation indicators) which may include glide-path/slope deviation. NDB (non-directional or locator beacon systems), TACAN, LORAN, GPS (other locator systems). In addition various landing assistance systems may be used such as: land based ILS (instrument assist landing system); ship based ICLS (instrument assist carrier landing system); GPWS and EGPWS (ground proximity warning systems); TCAS (traffic collision avoidance system); AoA or AoAS (angle of attack systems); ADS-B (air dependant surveillance broadcast); targeting view systems). The inputs may also include performance related measures/sensors such as: cockpit or cabin temperature pressure oxygen vibration component analysis, engine and instrument settings and performance monitoring sensors, yaw damper system setting and performance monitoring systems.

The vehicle centric outputs 230 may include sensors 232 which may be connected to the CPU 210 via a sensor interface 234 with or without a preprocessor 236. For aircraft the vehicle centric inputs 230 may include: Alerting systems which provide the human user information about the status of the aircraft; Auto Pilot which controls flight of the aircraft; GLOC (gravity induced loss of consciousness) systems which activates an auto pilot which controls flight of the aircraft; GPW (Ground proximity warning) systems which alert the human user of breach of a soft deck and in extreme cases invokes an auto pilot which plots a recovery path and takes control of the aircraft. Return home loss of link systems will either take over control of the aircraft and put it into a holding pattern or direct the aircraft to a home (or just a safer location). The vehicle centric output for an aircraft typically would also include output to the onboard flight and munitions delivery system associated with the aircrafts functions such as directing cannon fire or firing, launch and release of rockets.

The human centric inputs passive 240 may include sensors 242 which may be connected to the CPU 210 via a sensor interface 244 with or without a preprocessor 246. These human centric inputs passive 240 may include the aforementioned biometric information and information concerning the human user's environment.

The human centric inputs active 250 may include sensors 252 which may be connected to the CPU 210 via a sensor interface 254 with or without a preprocessor 256. These human centric inputs active 250 may include: manipulation of control devices such as the stick/wheel, pedals and power or thrust controls. It may also include biometric readings such as eye movement which the human user intentionally uses to control flight or targeting systems.

The human centric outputs 260 may include devices 262 which may be connected to the CPU 210 via an interface 264 with or without a preprocessor. These human centric outputs 260 may include: instrument panels or displays which may be in a dashboard configuration and/or a heads up display, or HMD (helmet mounted display; eyewear display; hepatic actuators intended to give hepatic feedback to the human user; EVS systems (enhanced vision synthetic).

It should be understood that though the inputs and outputs have been so divided. Various avionics subsystems may share inputs and outputs. For example the present invention and a targeting system may share the same visual display. Various avionics subsystems may also provide processing—the results of which may provide inputs to other avionics subsystems.

Figure 3:
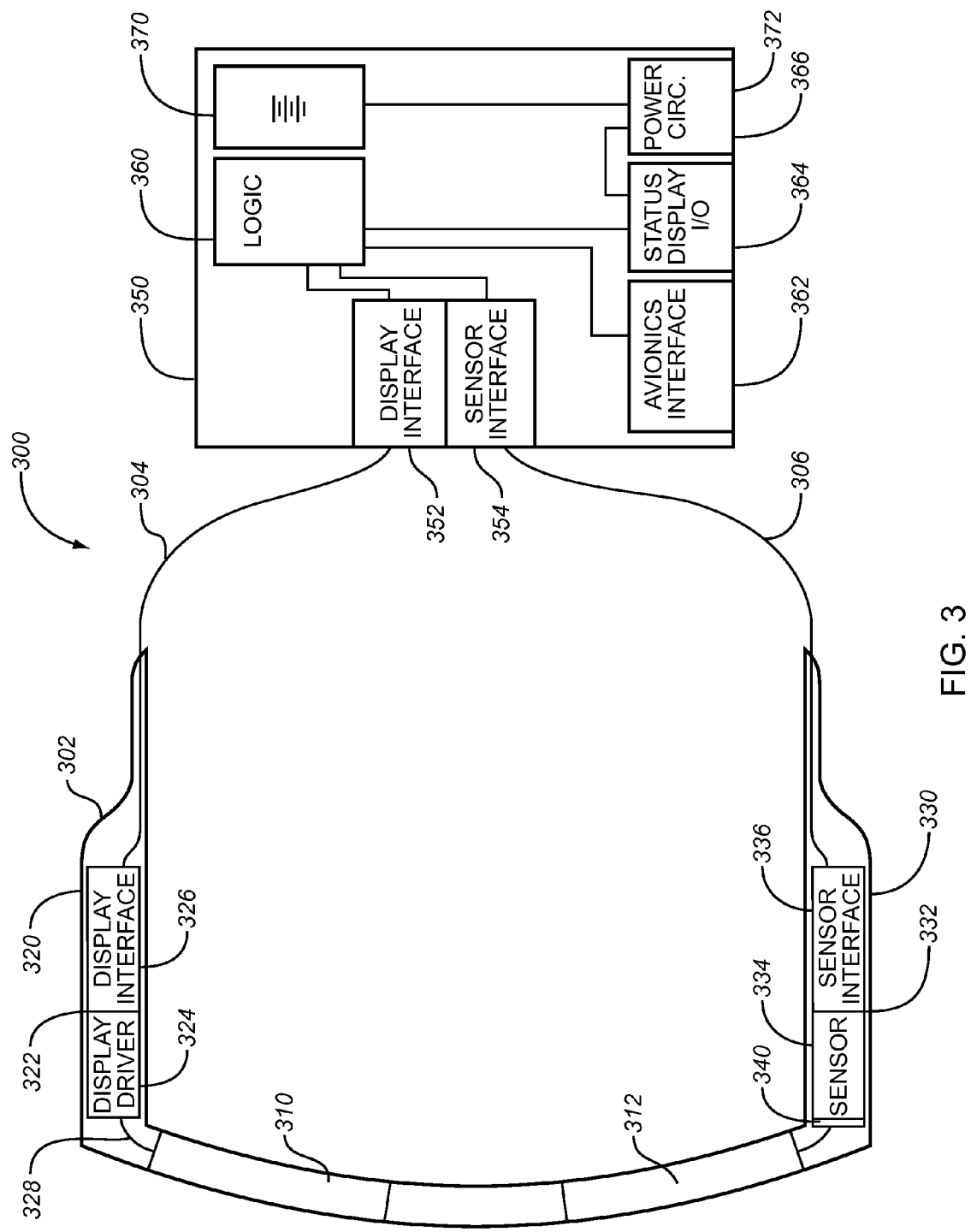
FIG. 3 illustrates a monocular example of an avionics subsystem implementation of the present system.

FIG. 3 is an illustration of major hardware components of an avionics subsystem 300 which has proven to prevent, avoid, ameliorate, and/or quickly resolve/correct SD/MS symptoms. The embodiment illustrated in FIG. 3 takes the form of a pair of eyewear glasses 302 to be worn by the user (not shown) electrically connected 304, 306 to a logic and power dongle 350. The embodiment illustrated in FIG. 3 is of a monocular system: so called because the eyewear has a right lens set 310 which incorporates a digital display and a left lens set 312 which does not. The glasses include a right temple 320 and a left temple 330. The right temple incorporates an electric control and communication circuitry which takes the form of a circuit board 322. In this embodiment the right temple 320 circuitry board 322 includes a display driver 324 for driving the display in the right lens set 310. It also includes display interface circuitry 326 for receiving a display signal from the dongle 350 and generating status information back to the dongle. In the embodiment illustrated the display driver circuitry 324 communicates with the display 310 via an electrical connection 328.

In the embodiment illustrated in FIG. 3 the left temple 330 also incorporates an electronic circuitry which takes the form of a circuit board 332. The circuitry on this circuit board 332 includes sensor circuitry 334 and sensor interface circuitry which communicates with the dongle 350. In some embodiments the sensor interface may include circuitry for doing sensor data preprocessing. In the embodiment illustrated the sensor circuitry includes microelectromechanical system (MEMS) chip(s) (sometimes referred to as micromachines and may sometimes take the form of NEMS (nanoelectromechanical systems). In the embodiments such as the one illustrated in FIG. 3, the applicant used two chips which sense inertial changes and together provided six degrees of freedom: three degrees representing rotation on three orthogonal axis and three representing inertial changes along each of the three axes. For many applications only three degrees of freedom may be required to gather and track the necessary data to generate the symbology. In a limited set of applications, it may be possible to incorporate aspects of the present inventive system with less degrees of freedom if the environment only provides inertial changes and is limited to a single two dimensional plane rather than a three dimensional space. In successful embodiments manufactured by the applicant, inertial sensors that detected both gyro type and accelerometer type of inertial sensors.

In the embodiment illustrated in FIG. 3, the dongle 350 includes communications circuitry, logic circuitry and power management circuitry. Those skilled in the art will appreciate that in an implementation of the embodiment illustrated in FIG. 3 two or more circuit boards can be employed: communications and logic on one board and power management on a second. The circuitry includes communications interface circuitry 352 and 354 for communications with the sensor board 334 and display driver 324 via communication links 304 and 306. The communications interfaces 326/352 and 336/354 interface communications with a central logic processor 360. The logic processor processes the sensor data from the sensors 340 and generates graphics information to be displayed on the display 310. Though not shown, the logic processor employees firmware programs and/or memory for storing software programs. The logic circuitry also has access to an avionics communications interface 362 to get information from other avionics systems/subsystems and sending information to the avionics systems/subsystems.

The dongle 350 also includes power management circuitry 366 which receives power from a charging port 372 and which manages and distributes power to charge a battery 370 and for use by all components/boards requiring electric power. The power circuitry 366 is also connected to status display circuitry 364. The status display circuitry 364 is also connected to communicate with the logic circuitry 360.

Figure 4:
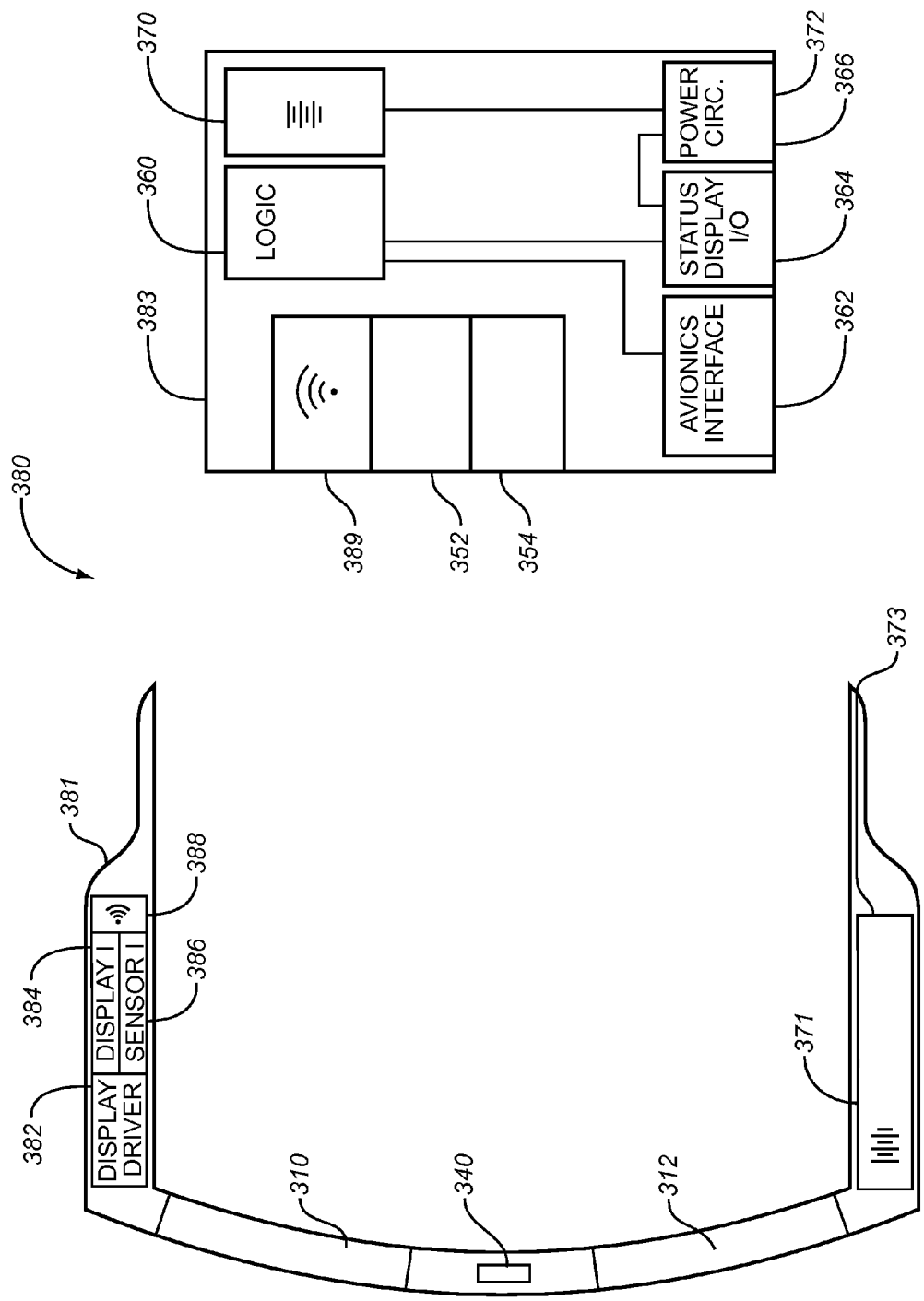
FIG. 4 illustrates an alternative embodiment of an avionics subsystem implementation of the present system.

FIG. 4 illustrates an alternative embodiment 380 of the avionics subsystem. This embodiment employs a display in each lens set 310 and 311. This embodiment may be employed in either monocular or binocular modes. In monocular mode, graphics are displayed on only one display 310 or 311 and presented only to one eye as with the embodiment 300 in FIG. 3. In binocular mode graphics are displayed on both displays. In binocular mode the same graphics may be displayed to both eyes or different information can be presented to each eye. In binocular mode it is possible to project the graphics as a three dimensional image by presenting each eye with different information and using different depths of field for the information displayed, if desired.

In embodiment 380 the driver(s) for both displays 382 are located on one temple side of the headset 381. In embodiments where a binocular mode presents the same information to each eye only one display driver is necessary. If the displays do not present the same information multiple display drivers may be necessary. In embodiment 380 the inertial sensors 340 are mounted in the bridge of the headset 381 which would present over the nose between the eyes of the user. In this embodiment the sensors circuitry also resides on the same temple side of the headset 381 as the display driver 382.

The embodiment 380 in FIG. 4 also differs from the embodiment 300 in FIG. 3 in that embodiment 380 includes wireless communication link 388 and 389 between the head set 381 and the dongle 383. A myriad of wireless communication links are suitable: such as blue tooth for example. A battery or batteries 371 reside in the opposite temple side of the head set. The battery can be charged via a charging port 373. The battery charging and conditioning circuitry reside in the charger (not shown). The batter(ies) 371 and inertial sensors 340 are electrically connected to the display driver 382, display driver interface 384, sensor circuitry 386 and headset wireless com 388 via electrical conductors (not shown) in the frame of the headset 381.

Figure 5:
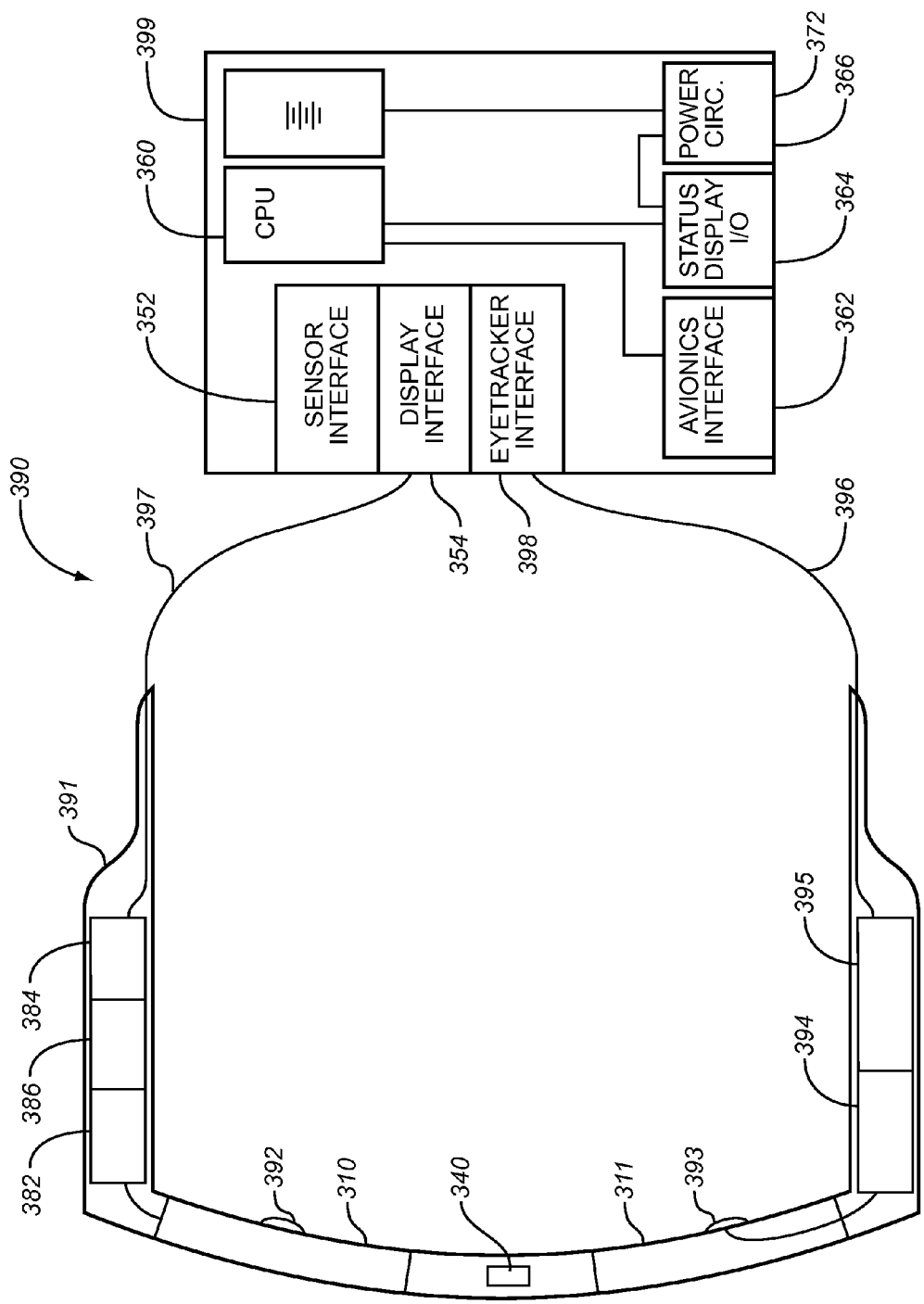
FIG. 5 illustrates a binocular alternative embodiment of an avionic subsystem implementation of the present system.

FIG. 5 illustrates yet a further embodiment 390 of an eyeglass headwear 391 implementation of the avionics subsystem. This embodiment further employs the use of eye sensors 392, 393. In one embodiment these sensor 392, 393 take the form of video cameras, which records images of the user's eyes as they move during use of the system. The video cameras are controlled by camera driver circuitry 394 and video interface circuitry 395 which interfaces with video interface circuitry 398 in the logic/power dongle 399 via umbilical electrical connection 396. The logic circuitry in the dongle 399 monitors ocular parameters like eye vertical (up and down) and horizontal (left and right), combined vertical and horizontal, and rotational eye movement and pupil dilation. This embodiment also includes inertial sensors 340 in the bridge of the headwear 391 and associated sensor circuitry 386 and interface circuitry 384 for interfacing with the logic and power dongle 399 via electrical connection umbilical 397. The embodiment also includes two displays in lens sets 310, 311, which are driven by video driver(s) 382 and interface with the logic/power dongle 399 with interface circuitry 384 via electrical connection umbilical 397.

Figure 6:
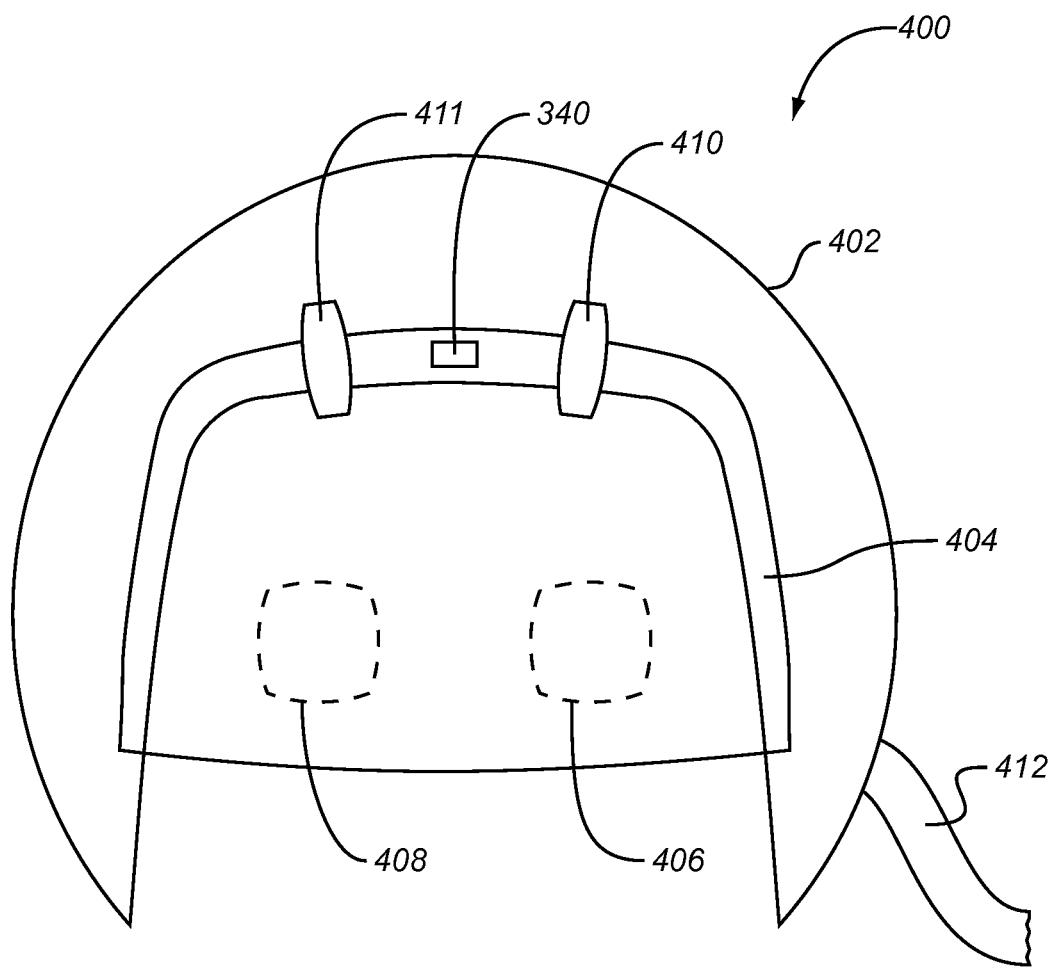
FIG. 6 illustrates a HMD alternative embodiment of an avionic subsystem implementation of the present system.

FIG. 6 illustrates a HMD (helmet mounted display) embodiment 400 of the headwear portion of an avionics subsystem. This embodiment includes a helmet 402 with a visor 404 onto which data can be displayed in display regions 406 and 408. The helmet 402 is also configured with eye sensors 410 and 411 which track ocular parameters such as pupil size and eye movement. The inertial sensors 340 are also helmet mounted. The element connected to the other avionics systems and subsystems via an umbilical 412 that contains electrical and optical conduits (not shown) for communication. For avionics applications of the user stabilization system taught herein, the HMD embodiment of the headwear portion of the subsystem is preferable for fighter applications such as for the $5^{th}$ Generation Fighters where helmets are traditionally used. The eyeglass embodiments illustrated in FIG. 3, FIG. 4 and FIG. 5 may be better suited for what is sometimes called shirt-sleeve environment applications: both airborne and terrestrial.

Figure 7:
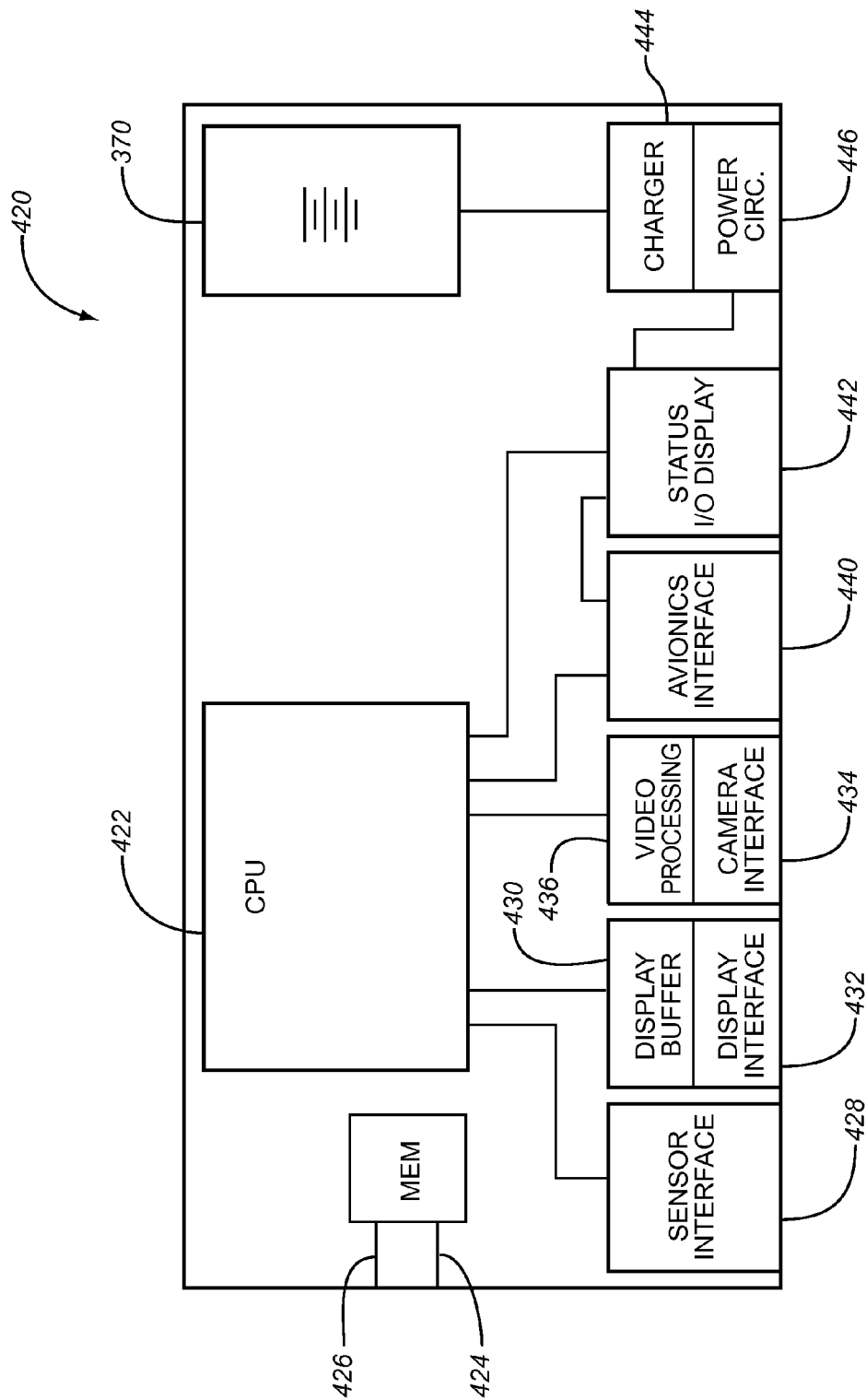
FIG. 7 illustrates an embodiment of an implementation of a logic dongle.

FIG. 7 illustrates an embodiment of a logic and power dongle 420 which may be used with the HMD. The dongle includes a central processor 422 which has access to memory 424 on which programs are stored. In alternative embodiments the programs may be hard coded into the hardware processor. However, in the embodiment shown the programs are downloadable via a programming link 426. The CPU 422 receives information from the inertial sensor interface 428 and the avionics interface 440. The CPU provides output to the display interface 432 which includes a display buffer 430 and the avionics interface 440. CPU 422 also receives information from a video image processor 436, which processes digital video images of the users eye(s) via the digital camera interface 434. To a limited extent the CPU 422 also provides output to the sensor interface 428 for calibrating and resetting the sensors. The CPU 422 also receives and sends information to the status display 442 which also includes user inputs (not shown) for turning on the power and resetting/calibrating the inertial sensor circuitry. The dongle 420 also includes power control circuitry for receiving monitoring distributing electric power which includes battery charging circuitry 444 for charging a system battery 370.

In a further embodiment the logic and power dongle 420 may be incorporated in the helmet in which case the battery 370 and battery charger circuitry 444 may not be necessary since power will be supplied through the HMD umbilical.

Figure 8:
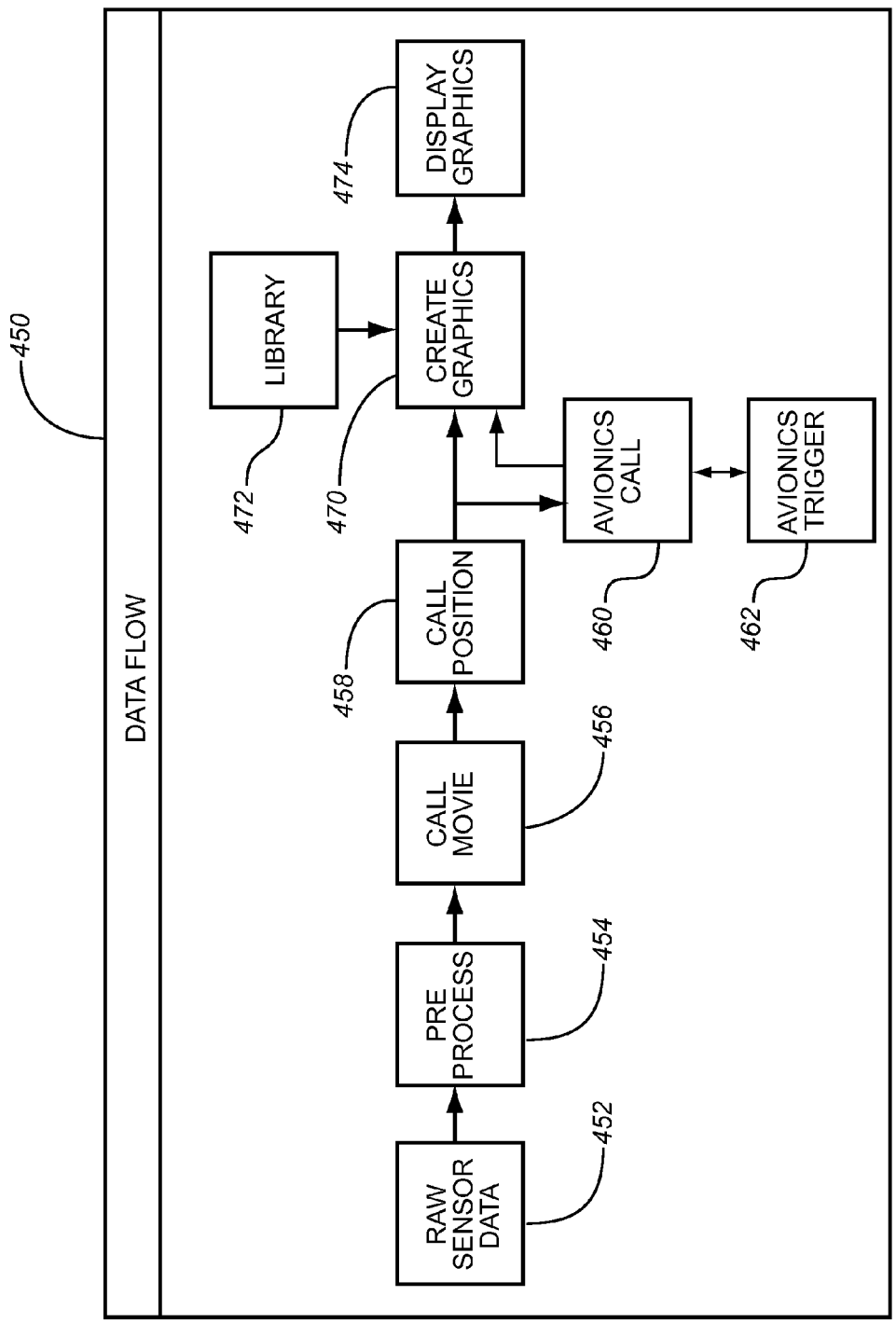
FIG. 8 illustrates an embodiment of data flow in the avionics subsystem.

FIG. 8 illustrates the data flow 450 of the avionics subsystem. In this illustration data flow 450 begins with the raw data generated by the inertial sensors 452. The sensor generated raw data 452 is extracted by and preprocessed into digital form 454. The digital data is further processed to calculate acceleration from which both movement and position are calculated 456, 458. This information is then further processed 460 in combination with information from other avionics subsystems 462 to generate the information needed to generate the graphics 470 using a graphics library 472 to be displayed 474 to the user.

Figure 9:
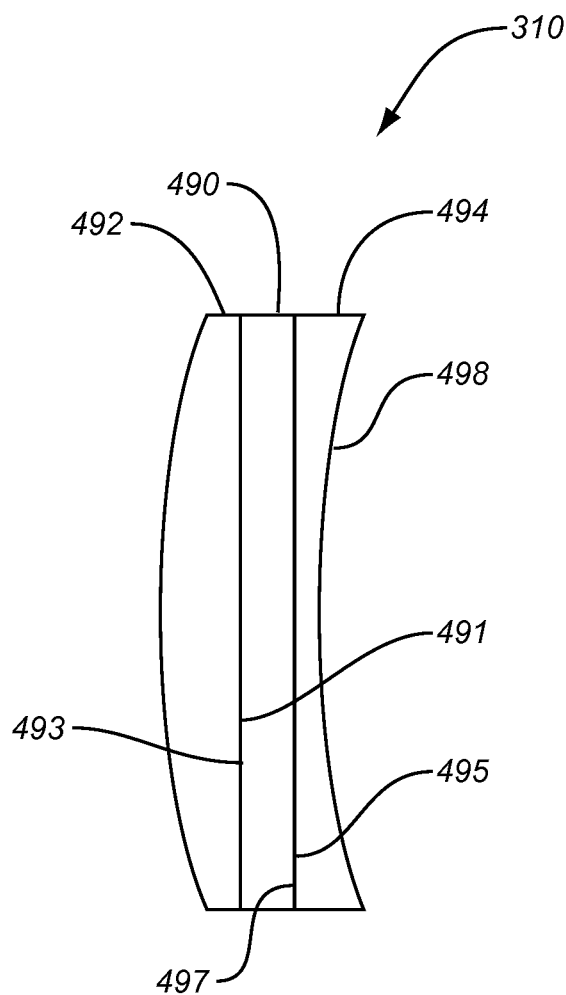
FIG. 9 illustrates an embodiment of a lens set implementation of the display.

FIG. 9 illustrates in greater detail and embodiment o the display lens sets 310, 311 (not shown). This embodiment 310 contains three components 490, 492 and 494. The central components 490 are digital displays. A myriad of display technologies are suitable for different applications. Examples of such technologies include but are not limited to light emitting diode (LED), organic light emitting diode (OLED), Flexible OLEDs and liquid crystal on silicon (LCOS) and wave guide array technologies or other displays such as low temperature Poly Silicon (LTPS) and excimer laser annealing (ELA) displays. Different applications may call for different choices of display technology. The factors to consider are the pixel size, the lumen output, the efficiency or power required to achieve the desired lumen output. For avionics requiring daytime usage a higher light output is necessary. Therefore for such an embodiment the applicants found an arrayed waveguide display (AWD) to be particularly suitable to obtain a suitable lumen output with adequate resolution in a eyeglass mounted display.

The outer lenses 492 and 494 combine to create the desired focal plane for the display. In the preferred embodiment the desired focal length for the display is approximately two to three feet or about a meter. In other embodiments, other focal lengths can be used up to infinity (focal lengths of about fifteen to twenty (15-20) feet and beyond serve as effectively infinity for the human eye). It is preferred that the mating surfaces 493, 491 and 497, 495 match to reduce the internal reflect between the components and so that if desired the components can be adhesed/glued together to further reduce internal reflections within and between the components. The embodiment illustrated in FIG. 9 employs flat mating surfaces 493, 491, 497, 495. This has been found to allow for relatively thin lenses. In this embodiment of a lens set it is possible to account for user specific vision correction by shaping the user facing surface 498 to the inside lens 494. In alternative embodiments other shaped mating surfaces may be employed. In further embodiments the display may be manufactured in a substrate which is thick enough to be ground so that the lens set is comprised of a single lens. In further embodiments it might be desirable to include thin film coatings on the lenses which would optimize their use in particular conditions such as night vision, in daylight or prescription requirements.

Symbology. Of critical importance to success of the system is the symbology of the cues provided to the user to prevent, avoid, ameliorate spatial disorientation and motion sickness. Not only is the information provided important but experience demonstrates that how the information is provided is critical to successful use of the system. The following describe embodiments of symbology that has been demonstrated to be successful. Many factors are important to the success of the cue symbology such as, shape(s), color(s) and dynamic mechanization(s) of the symbology as used in various embodiments for various applications.

The particular combinations of symbology and symbology elements and functions may vary. The variety may in whole or in part be driven by the application in which the embodiment is intended for use. For example symbology appropriate in particular medical or other military applications are likely to differ from symbology appropriate for aviation applications. With even more granularity different symbology may be appropriate for two different medical applications. Similarly different symbology may be appropriate for two different military applications such as driving a jet fighter verses flying a drone remotely or driving a tank. Nevertheless some of the features are common.

Figure 10:
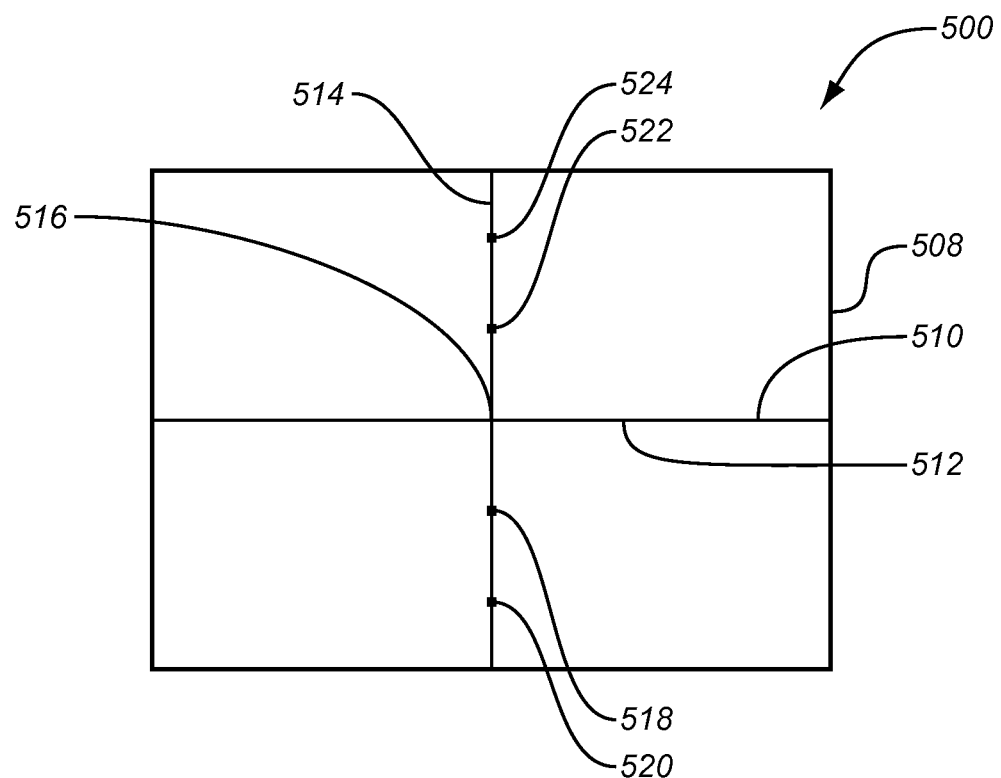
FIG. 10 illustrates and embodiment of a Head Attitude Scale (HAS)

Head-Attitude Scale (HAS). An embodiment of a head-attitude scale (HAS) 510 with in a Field of View (FOV) 508 is illustrated in FIG. 10. In some embodiments, the HAS 510 is a magenta-colored Cartesian graph with equal-length x-(horizontal) axis 512 and y-(vertical) axis 514 that intersect in their respective centers at the graph origin (vertex) 516. In some embodiments the HAS 510 is centered in, and extends to the limits of, the display field-of-view FOV 508 as depicted in FIG. 10.

In this embodiment, the horizontal axis 512 represents a range of plus or minus One Hundred and Eighty degrees (±180°) of lateral rotation (yaw) from the vertex 516 and is not indexed. The vertical axis 514 presents a range of plus or minus plus or minus Ninety degrees (±90°) of vertical rotation (pitch) and has four short indices 518, 522 and 520, 524 respectively representing plus or minus Forty-Five degrees ±45° and plus or minus Ninety degrees ±90° pitch displacement from the vertex 516. In this embodiment, the vertical axis 514 extends past the useable scale plus or minus Ninety degrees (±90°) 520 and 524 in order to provide continued visual stimulation and stability in the vertical plane to the limits of the FOV 508. No symbols are displayed above or below the plus or minus Ninety degrees ±90° indices on the HAS 510 vertical axis 514.

Figure 11:
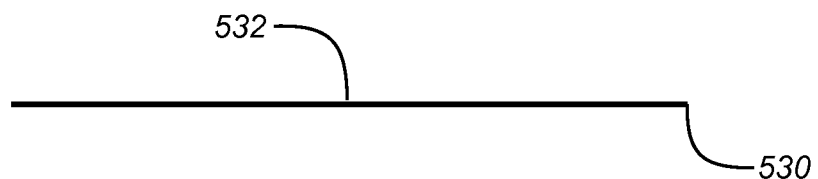
FIG. 11 illustrates an embodiment of a Pitch/Roll Indicator (PRI)
Figure 12:
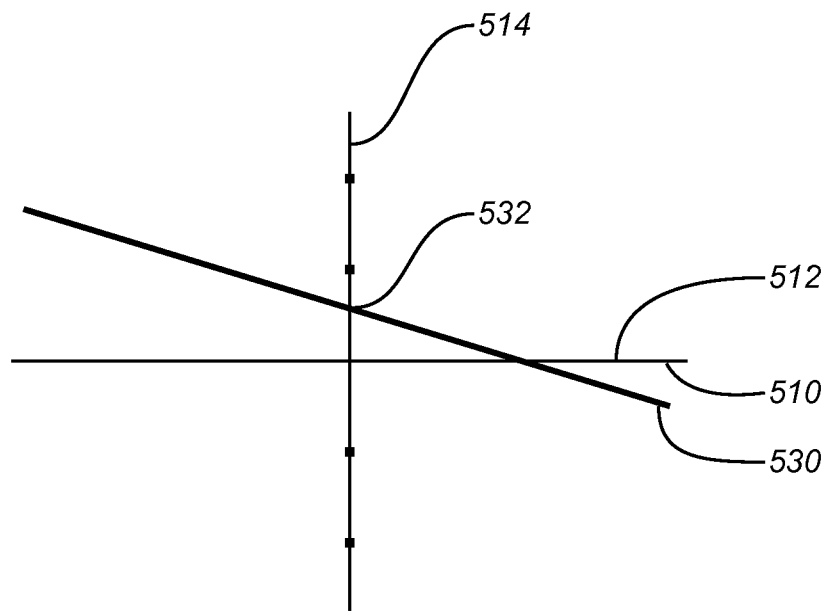
FIG. 12 illustrates an embodiment of a Pitch/Roll Indicator (PRI) of FIG. 11 in conjunction with the HAS of FIG. 10.

Pitch/Roll Indicator (PRI). An embodiment of a Pitch/Roll Indicator (PRI) 530 is illustrated in FIG. 11 and FIG. 12. In some embodiments this indicator is a tangerine-colored line with a length approximately one-third the length of the HAS 510 horizontal axis 512. The PRI 530 is bisected by, moves vertically along, and rotates (tilts) about the HAS 510 vertical axis 514. Consequently, the PRI 530 represents the pitch and roll attitude of the users head relative to the real-world horizon and as referenced against the HAS 510.

Figure 13:
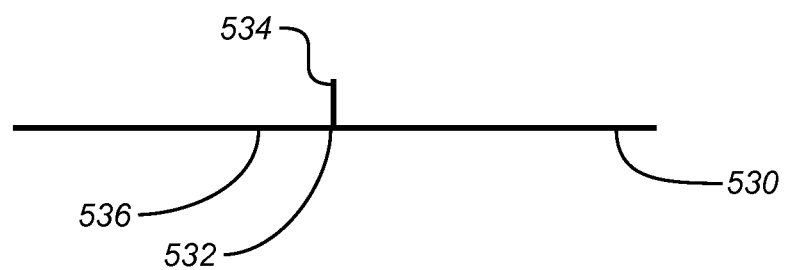
FIG. 13 illustrates an alternative embodiment of a Pitch/Roll Indicator (PRI) with a vertical fin.
Figure 14:
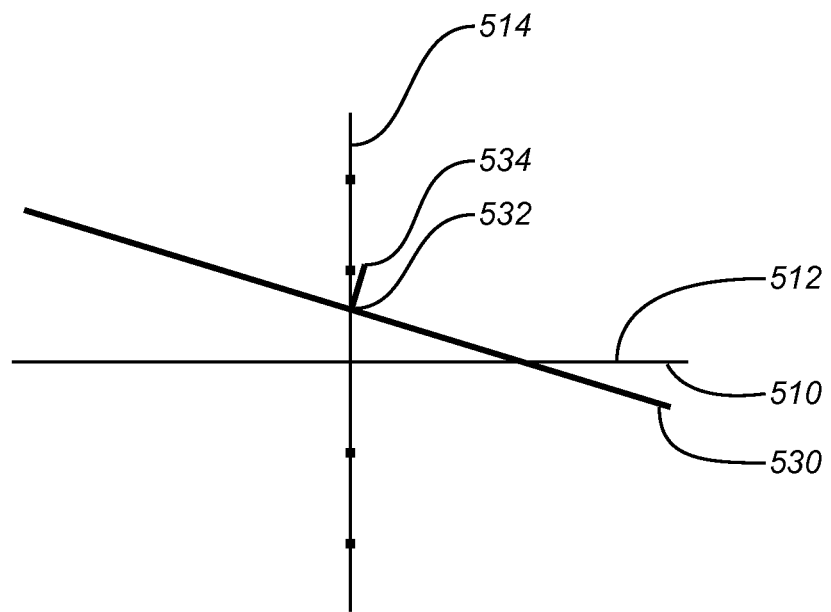
FIG. 14 illustrates an embodiment of a Pitch/Roll Indicator (PRI) of FIG. 13 in conjunction with the HAS of FIG. 10.

FIG. 13 and FIG. 14 illustrate an alternative and in many cases preferred embodiment of the Pitch/Roll Indicator (PRI) 530 is comprised of two perpendicular lines 531 and 534 with the shorter of the two lines 534 placed on top and in the center 532 of the longer line 531. In this embodiment the longer line (pitch/roll bar) 531 is of the same dimensions as the as the PRI in FIG. 11 and FIG. 12 and is oriented the same relative to the HAS 510 vertical axis 514 to indicate head displacement in the pitch and roll axis. The shorter line (vertical fin) 534 presents the direction toward the top of the user's head and can be considered to point in the direction of the lift vector of an aircraft when the wearer is sitting upright in the seat. In this embodiment, the vertical fin's 534 height is approximately one-ninth the length of the roll bar. 531

In this embodiment the PRI 530 is tangerine-colored when roll attitude is less than or equal to plus or minus Ninety degrees (±90°) as referenced to the HAS 510 vertical axis 514 and red colored when roll attitude is greater than plus or minus Ninety degrees (±90°).

In the embodiments illustrated in FIG. 11, FIG. 12, FIG. 13, and FIG. 14, the PRI 530 is an "outside-in" presentation and represents the wearer's head position as if viewed from a distance from (or outside) the head. For example, head tilt to the right is presented as a right-tilted PRI 530 in relation to the vertical axis 514 of the HAS 510 (ie vertical fin 534 "points" to the right of the vertical axis 514). Similarly, an upward tilt of the head is displayed by positioning the PRI 530 on the positive side of the HAS 510 scale relative to the horizontal axis 514 as illustrated in both FIG. 12 and FIG. 14.

In both illustrated embodiments, the PRI 530 rotation is conformal to the real-world (outside scene) in roll, but not in pitch. For example, Thirty degrees (30°) of rotation to the right is displayed as Thirty degrees (30°) roll, while PRI elevation (climb) and depression (dive) are compressed. In other embodiments the angular range of view may differ as may the compression ratio. In yet other embodiments the compression ratio may not be linear. In both models the PRI is limited vertically when it reaches the plus or minus Ninety degrees (±90°) index on the HAS. Some embodiments rotate a maximum of One Hundred and Eight degrees (180°), while the other embodiments may rotate Three Hundred and Sixty degrees (360°).

Figure 15:
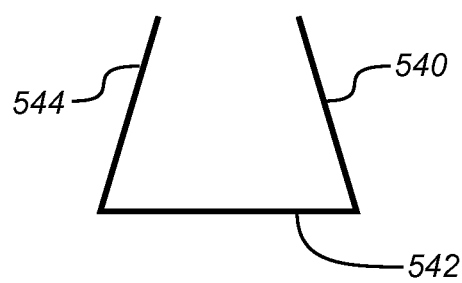
FIG. 15 illustrates an embodiment of a Head-Rotation/Yaw Indicator (Yaw Indicator)

Head-Rotation/Yaw Indicator (HRI). An embodiment of a Head-Rotation/Yaw Indicator 540 is illustrated in FIG. 15 as an open-ended, three-sided trapezoid. In an actual embodiment the HRI 540 is tangerine-colored.

Figure 16:
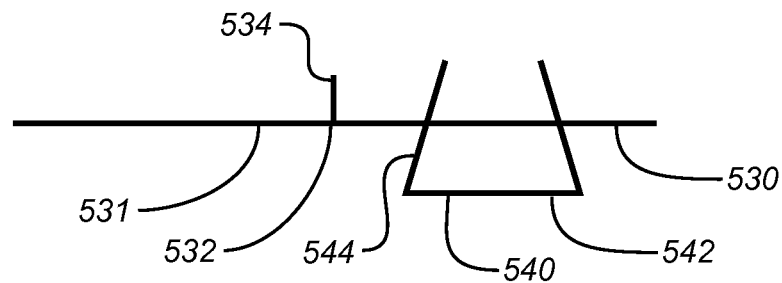
FIG. 16 illustrates an embodiment of the Head-Rotation/Yaw Indicator of FIG. 15 in conjunction with the Pitch Role Indicator of FIG. 13.

As illustrated in FIG. 16, the HRI 540 "slides" the length of the PRI 530 as the user's head is rotated left or right of straight ahead about the central axis of the user's head. In the embodiment illustrated, the HRI 540 extends above and below the pitch/roll bar 531 of the PRI 530, but its height is less than the height of the vertical fin 534. The center of the HRI trapezoid remains coincident with the center of the PRI 530 roll bar 531 during pitch changes, while it moves independently along the PRI roll bar 531 when the wearer's head position changes in lateral rotation. The lateral position of the HRI remains constant as long as the wearer's head is rotated away from straight ahead in relation to his or her body.

In alternative embodiments the HRI also represents the rotational position of the users head relative to his trunk. In avionics applications this latter embodiment has proven to be more effective for some users.

Figure 17:
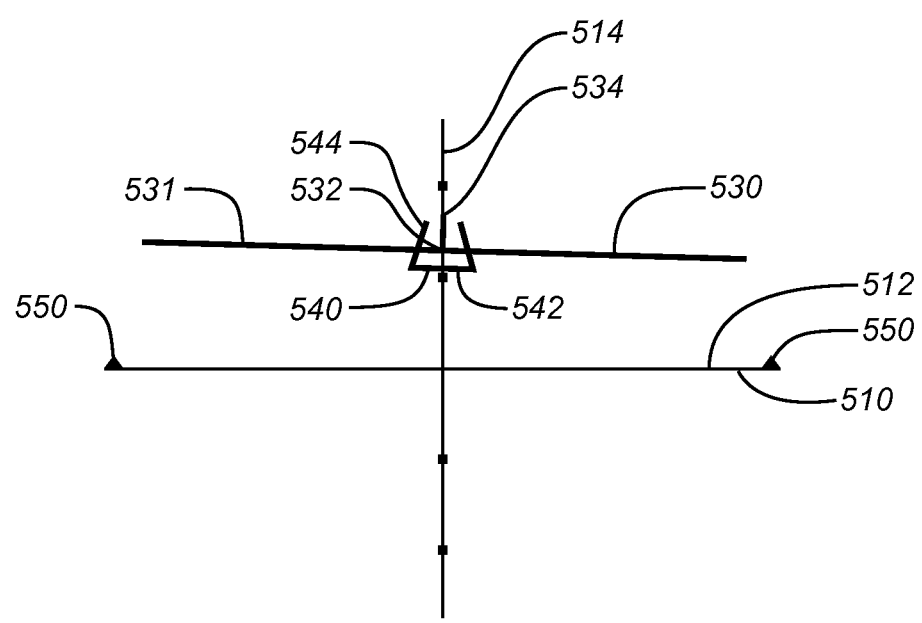
FIG. 17 illustrates an embodiment of the Head-Rotation/Yaw Indicator of FIG. 15 in conjunction with the Pitch Role Indicator of FIG. 13 in further conjunction with the HAS of FIG. 10.
Figure 18:
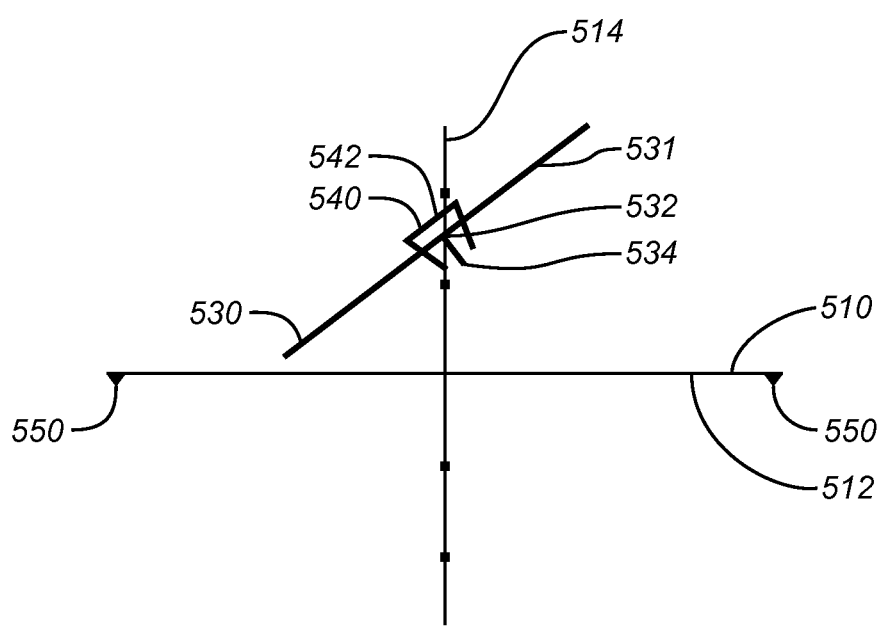
FIG. 18 illustrates the embodiment of symbology FIG. 17 reflecting different positional circumstances.

Upright/Inverted (UI) Triangles. An embodiment of upright/inverted indicators (UI) are triangles 550 on the ends of the HAS 510 horizontal axis 512. To indicate upright, the triangles 550 are green in color, and the apexes point upward as shown in FIG. 17. Upright is determined by the PRI 530 indicating less than or equal to ±90° of roll as referenced to the HAS 510 vertical axis 514. When roll is greater than ±90°, the triangles change color to red, and the apexes point downward, indicating inverted as shown in FIG. 18

Focal Length. As previously described, the preferred embodiment the display of the symbology suite focused at a range of approximately two (2) feet in contrast to 15 feet/infinity. Testing revealed this focal length made the symbology more effective in controlling SD/MS and provided a recognizable contrast in symbology from the flight control and fire control targeting symbology associated with HMD and HUD displays.

Colors. The colors cited above where selected based on a particular avionics application. The colors were selected both for their visibility and so that they do not conflict with other symbology presented to the user by other avionics subsystems such as a targeting system. In other applications other colors may be desirable. For example for systems employed for particular use in the dark such as night time, it may be desirable to use green colors in order to maintain night vision. In further embodiments the focal lengths may vary with the symbology. For example, some symbology may be displayed at different focal lengths than other symbology.

Offset Vs. Bore Sight Display. In some embodiments, the location of the symbology within the field of view is programmable. For example, the location of the symbology may be offset from the center bore sight to allow the user to better see through the display and to enhance compatibility with other optical displays such as HMD or night vision equipment and symbology such as fire control targeting symbology. In one embodiment the symbology is presented off bore sight up Ten to Fifteen degrees (10-15°) and left about Thirty to Forty-Five degrees (30-45°) to one side or the other (preferably to the left for the left eye or to the right for the right eye). When the symbology is displayed off bore sight, it is shrunk to fit. In some embodiments, the symbology can still however be set on bore-sight taking the same view-space of his other instruments if desired by the user.

In further embodiments the symbology remains off bore sight during normal operation. However if the avionics sensors experiencing triggering events that suggest that the pilot has begun to experience or may begin to experience spatial disorientation, the symbology increases in size as it moves from off bore sight to on bore sight. In such events, other parameters of the symbology may also be enhanced such as the thickness and color or color intensity. In some embodiments the enhancement may be escalated as the indications of spatial disorientation increase for potential to actual to loss of control. In some embodiments, as the situation escalates, other symbology presented to the user may be overridden to give the user a chance to reorient with out the disorienting stimulation of the other symbology. For example, if the pilot is experiencing nystagmus the fire control targeting symbology may be removed in favor of the reorientation symbology described herein. In further embodiments the user is provided with the option to declutter or deescalate the enhancement of the symbology presentation to the user.

Monocular Display. A avionics subsystem with a monocular display has shown to be effective in controlling SD/MS while reducing power requirements and the size of visual "real estate" required on our glasses and HMD displays. This design also allows for reduced pixilation and computational requirements enhancing reliability and miniaturization. It can be presented in a binocular display if required.

3-D Display. The unique display technology created by the video engine and optics allows for the presentation of a 3 dimensional display if needed or desired and facilitates the interface with other human performance improvement technologies.

Eye Tracker. As previously described the eye tracking sensors employed in embodiments of the invention employ the use of video cameras. Programs process the images taken from the video cameras to look for certain types of eye movement characteristics. For example, the eye tracker programs look for eye closure rates and duration of eye closure, which are indicative of spatial disorientation, GLOC or other causes of user disabilities. The programs also look for abnormal eye movements indicative of nystagmus which is highly indicative of spatial disorientation. The system detects both linear (vertical horizontal or between vertical and horizontal) and tortional nystagmus. These detections are then shared with and integrated with other avionics subsystems.

Auto GCAS and Anti GLOC. Two subsystems that the spatial disorientation system integrates are the Auto Ground Collision Avoidance System (A-GCAS) and the Anti G Induced Loss of Consciousness system (A-GLOC). If the eye tracker detects eye closure of a predefined extended duration or had detected nystagmus for an extended period, the pilot will be warned of the detection and the eminent seizure of control of the vehicle and provided with an opportunity to override vehicle control. If the user does not override, then the A-GCAS or A-GLOC systems will take control of the aircraft typically returning the vehicle to a safe attitude and possible directing the vehicle toward a home location.

Augmented Reality. Augmented Reality systems use sensors to analyze the scene being viewed by the user, enhance the see through visual display using information contained in an internal database and special use algorithms and then display enhanced information to fill in information not actually visible to the wearer. This enhancement may be augmented by activating the SD/MS display symbology based on the optical tracker inputs and overlay ground position awareness or g information. In alternative embodiments the augmented reality provided to the user may be views of the aircraft position in space such as external or "God's eye view" or predicted flight path together with the SD/MS display symbology.

Virtual Control Interface. In this use the optical tracker analyzes eye movements for a special use algorithm and provides flight/operator control inputs to the vehicular system and/or fire control inputs to a combat or law enforcement system.

In the preferred embodiment of the SD/MS system integrated with other avionics systems, the SD/MS system monitors the flight conditions such as direction and change in direction, speed, vibration, flight time, visibility etc. This information is processed and indexed to a level of how provocative the environment is and has been to causing SD/MS. If the environment passes a threshold the SD/MS display symbology may be activated or enhanced depending on the level of provocation. These thresholds may be user specific. In further embodiments the system can be configured differently for different users based on their predetermined tolerance level.

Gaming Interface. In this use the optical tracker analyzes eye movements for a special use algorithm and provides gaming control inputs to the game controller and/or provide SD/MS display if the associated eye movements dictated its display.

Applicable Applications for the SD/MS avoidance system. The user worn SD/MS display symbology performance enhancement system has application in many fields outside the highly motion provocative military applications, such as non-military motion provocative environments, medical rehabilitation and consumer use. The modular and miniature design of the eye glass subsystem allows the use in a much larger field of use, including vehicular travel (land, sea and air), medical rehabilitation, space travel, microgravity, and space and/or microgravity return rehabilitation, consumer use and integration with operator control interfaces.

Vehicular Travel. The most obvious use for a technology to prevent SD/MS is in an environment where movement alters our normal sense of perception and visual cues such as moving in a variety of vehicles.

High Performance Fighters—Legacy Systems. There are uses for this technology in the systems that still use helmets but do not use HMD technology—the number of legacy systems far exceeds the HMD used and will continue for a number of years. By integrating our technology into pilot eyewear and HMDs, we can improve mission-effectiveness and human performance, while decreasing the probability for loss of aircraft and life. Additionally, our technology will help solve MS in military pilot training Motion sickness significantly impacts the student's physical performance by reducing cognitive and motor abilities. Students routinely leave pilot training due to their continual battle with MS. Using the present systems to effectively combat MS in flight students will: 1) improve pilot performance, enabling them to focus on and master tasks more quickly; 2) reduce student pilot attrition rates due to "active" MS (vomiting); and 3) increased student pilot confidence which leads to better pilot training and increased retention. The SD/MS avoidance system can obtain similar results for crew use within tactical and strategic Air Force operations.

High Performance Fighters—Helmet Mounted Display (HMD) Systems Users. The modular nature of our new software and firmware allows the integration of this technology into the already existing sensor and display suites associated with $4^{th}$ and $5^{th}$ generation fighter aircraft HMDs including JHMCS (Joint Helmet Mounted Cueing Systems) By integrating our technology into HMDs and JHMCSs, we can improve mission-effectiveness and human performance, while decreasing the probability for loss of aircraft and life. The near focused feature of our symbology, coloration and shape allow the technology to be effective while de-conflicting with aircraft control and targeting displays.

Tanker, Airlift, Support. We envision tanker, airlift and support aircraft as well a crew members who operate in the back of these vehicles will employ the eyeglass device to improve mission-effectiveness and human performance, while decreasing the probability for loss of aircraft and life.

Helicopter. Rotary wing aircraft are particularly capable of generating high motion provocative environments due to extreme vibration, the visual flash of the rotor blades in various lighting conditions and unique maneuvering capabilities.

Flash Vertigo. There are many case examples where helicopter operators/passengers have encountered extremely adverse physical effects due to the flickering or flashing of light through the rotating blades of the helicopter. Some of the most severe have resulted in epileptic fit, stroke and of course vertigo and MS. Use of the new technology is expected to greatly reduce the negative effects associated with the strobe effects of rotor wing vehicles.

Brown-out. Rotary wing operators often experience loss of visual cues and a sensation of downward velocity increase and/or disorientation when landing in blowing or loose sand environments. It is believed our technology will help alleviate the disorientation associated with the "brown out" phenomenon.

Naval, Shipboard Simulator Training. Naval aircrew members assigned aboard ships who engage in flight simulator training on those ships often are affected by motion sickness. This occurs because the motion of the ship and associated vestibular stimulus creates a mismatch with visual cues viewed in the simulator. Additionally the simulator results in a loss of visual cues regarding the shipboard environment. It is believed our technology will prevent motion sickness that occurs during ship board flight simulator training.

Naval, Aggravated Sea States. Sailors stationed aboard naval ships and merchant marine vessels have long been susceptible to motion sickness associated with the vessel movements that occur during aggravated sea states. It is estimated that nearly every person ever stationed aboard a marine vessel for a prolonged status has suffered mild to debilitating sea sickness. It is believed our technology will prevent/alleviate the symptoms of sea sickness aboard ships.

Counter Vertigo in Virtual Pilot Vehicle Interface. Operators of unmanned aerial systems routinely experience spatial disorientation due to limited visual cues in sensor control displays. Further, experiments using a virtual pilot vehicle control interface, where the pilot controlled the UAS based on visual cues derived directly through sensors (placing the point of view on the nose of the aircraft) versus via CRT control displays led to cases of SD and motion sickness. It is believed our technology will prevent SD/MS in both UAS PVI environments.

Civil and Military Flight Operations. SD/MS causes degradation of human performance (affecting cognitive and motor skills), with resultant loss of expensive equipment and human life. The Aviation Safety Foundation of the Aircraft Owners and Pilots Association indicates an aircraft accident or mishap attributed to SD occurs approximately every 11 days. These accidents have resulted in a fatality rate of 91% in the General Aviation (GA) community and a 69% fatality rate in the U.S. Military. From 1980-2000, the USAF experienced 1,087 aviation fatalities with over 14% (172) directly attributed to SD at a cost of over $1.54B.

Operators. There are over 650,000 civilian pilots in the United States alone. According to the FAA there is an estimated SD related mishap every 11 days in the US. Non-instrument rated pilots who fly into the clouds historically have 178 seconds before ground impact. It is believed our technology can provide the visual cues necessary to combat SD in the civil aircraft flight environment.

Passengers. Passengers in commercial air carriers, business and general aviation aircraft routinely experience motion sickness from vestibular upset and loss of visual cues. It is believed our technology can prevent the SD and MS for passengers aboard all type of civil aircraft.

Space Flight Operations—Micro-gravity. NASA reports that nearly every astronaut is stricken with "space sickness" associated with the loss of balance due to micro-gravity environments. The only remedy at this moment is drug therapy while stationed in space, a decidedly non-optimal solution. Additionally during training for space flight students aboard the zero-G flight simulator routinely experience motion sickness. It is expected out technology will remedy space sickness and by providing visual cues to offset the loss of proprioception and orientation due to loss of gravitation.

Space Re-entry Rehabilitation. Astronauts returning from extend space flights routinely have to learn to reorient themselves in the terrestrial environment. Motor and cognitive skills are often observed to be severely degraded during the re-acclimation period. This is due to the sudden reintroduction of gravitational cues and stimulus of proprioceptors. The time needed to re-acclimate to the terrestrial environment is about three days per week in space. It is expected our technology will greatly reduce the time to re-acclimate to the terrestrial environment by providing strong visual cues to help orientation in conjunction with the increase in cues provided by reintroduction of gravitation.

Medical Rehabilitation. Presently, 10 million patients receive balance (vertigo) therapy costing $1 billion annually. Reasons for treatment are due to disease affecting the vestibular organs, rehabilitation from surgery on the balance organs, recovery from trauma to the head and rehabilitation in patients learning to use prosthetics in the lower extremities. Clinical tests conducted by the inventor funded by the National Institutes of Health (NIH) resulted in 96% effectiveness in resolving balance issues associated with these various maladies.

Overcome Chronic Illness. Many patients with the NIH test group with chronic balance disorders were able to return to functionality after enduring years of other ineffective treatments. The visual display reduced the average number of clinical visits from 25 rehabilitation treatments to 5 and in several cases proved to be the only effective treatment the patient had ever experienced.

Recovery from Surgery. Within the NIGH test group, the visual display proved to reduce the average number of clinical visits from Twenty-Five (25) rehabilitation treatments to Five (5) and in several cases proved to be the only treatment effective.

Recovery from Trauma. Head trauma and injury to the inner ear often results temporary balance problems. The loss of proprioception with injuries to extremities can also result in loss of balance. In tests the visual display greatly shortened rehabilitation and recovery times and in some cases was the only treatment effective to aid recovery due to head trauma, vestibular injury and limb injury.

Rehabilitation using Prosthetics to Lower Extremities. Physicians associated with the US Army Center for the Intrepid, based at Brook Army Medical Center in San Antonio Tex. report that many soldiers who have suffered injury to the lower extremities or amputation have balance issue while learning to use prosthetics. This is due in part to loss of proprioception inputs associated with the loss of the limbs and new weight distribution associated with the prosthetics. It is hypothesized our technology will greatly shorten rehabilitation time by providing strong visual cues to offset the loss of sense of touch due to limb loss and aid balance while learning to use the new limbs.

Consumer Use. Our technology is deemed to be agnostic in that it can be integrated into a number of carriers and used to prevent SD/MS in nearly any environment where there is a loss of visual cues and or proactive motion. The latest design allows the application of our technology in a myriad of non-clinical, consumer focused activities. Numerous individuals are afflicted by SD and MS in a variety of activities, such as riding in automobiles or buses, taking ocean cruises, deep sea or sport fishing, etc.

Sports Applications. In nearly every sports activity that features the loss of visual cues or motion provocative environment such as sailing, rock climbing, and auto racing participant's remark on the loss of situation awareness, disorientation or occasional motion sickness. It is expected the use of our technology will prevent SD/MS in these environments by providing strong visual cues to counter the effects of sensory mismatch associated with these motion provocative environments.

Offshore Fishing. It is highly common for at least one person in the party of any recreational offshore fishing boat to become seasick. As already alluded above in the naval section, our technology is expected to be highly effective in the prevention and control of MS in person aboard small marine vessels.

Cruise ships. Of over Twelve and a half Million (12.6 million) passengers who cruise annually it is estimated greater than 20% become seasick. Our technology is expected to be highly effective in controlling MS associated with leisure ship board cruises.

Reading during Vehicular Travel. Many people become carsick when sitting in the back of a moving vehicle with reduced visual cues and increased vibration and even more still when attempting to read in this motion provocative environment. Our technology will provide strong visual cues to counteract the loss of peripheral visual cues and offset the effect of vibration in the ground transportation environment.

Theme Parks. It is highly common for tourists visiting theme parks to become disoriented or experience motion sickness riding them park rides. This is due to the nature of the attractions themselves that either generate extreme motion provocative environments or provide visual cues that have the same effect by showing extremely provocative visual displays. Our technology can prevent motion sickness by providing overriding visual cues that show the true orientation of the passenger with respect to the ground. The glasses are expected to be most effective in countering SD/MS in rides that use high fidelity visual displays since the passenger would be able to verify his/her actual position vice the suggested position from the visual display.

Gaming Applications. A number of modern electronic games feature a virtual control interface. These displays are often not see-through and present highly motion provocative visual displays. Our technology overlaid on the virtual gaming interface would counteract the lack of visual cues and show the gamer true position in space, thus lowering SD and improving situational awareness.

PDA Interface. Our technology carrier currently uses an umbilical that could plug into an i-Phone or i-Pod and could be upgraded in future generations using Bluetooth technology. Using either technique we have the capability to interface with Personal Data Assistants (PDAs). It is possible for the battery to be charged using the interface and for PDA information to be displayed on the glasses.

Adaptation to Various Carriers The modular nature of our sub components and software suite allow for the integration the SD/MS system into other head worn devices other than glasses, or HMD such as night vision equipment, binoculars, goggles, SCUBA masks and any other user worn device. The system can also be integrated with non-head worn display devices such as HUD which display information on a view screen.

While the disclosure has been described with respect to a limited number of embodiments, those skilled in the art, having benefit of this disclosure, will appreciate that other embodiments may be devised which do not depart from the scope of the disclosure as disclosed herein. The disclosure has been described in detail, it should be understood that various changes, substitutions and alterations can be made hereto without departing from the spirit and scope of the disclosure.

What is claimed is:

1. A system comprising:
a unit attachable to a person's head wherein the head-attachable unit further comprises:
an orientation sensing element responsive to pitch of the person's head and roll of the person's head wherein:
pitch represents a rotation about a first axis representing up and down movement of the person's face while the rear of the person's head moves in the opposite direction and roll represents rotation about a second axis perpendicular to the pitch axis in which the face rotates about the nose when looked at from the front;
the orientation sensing element comprises:
a circuit board;
interface circuitry;
communications circuitry;
logic circuitry;
a central processing unit;
a memory unit;
sensor data pre-processing circuitry; and
a micro-electro-mechanical system integrated circuit wherein the micro-electro-mechanical system further comprises an accelerometer;
an eye sensor comprising a video camera, wherein the video camera is responsive to:
eye closure;
changes in pupil size;
horizontal nystagmus detected as temporal involuntary horizontal eye movement caused by self-perceived motion sensation as a result of a physiological effect including one or more of vertigo, motion sickness, motion intolerance, or spatial disorientation due to sensory mismatch between the person's visual, vestibular, and proprioceptive organs;
vertical nystagmus detected as temporal involuntary vertical eye movement caused by self-perceived motion sensation as a result of a physiological effect including one or more of vertigo, motion sickness, motion intolerance, or spatial disorientation due to sensory mismatch between the person's visual, vestibular, and proprioceptive organs; and
torsional nystagmus detected as temporal involuntary eye rotation caused by self-perceived motion sensation as a result of a physiological effect including one or more of vertigo, motion sickness, motion intolerance, or spatial disorientation due to sensory mismatch between the person's visual, vestibular, and proprioceptive organs; and
a head-attachable display viewable by the person wherein the head-attachable display comprises:
a display driver;
a see-through region that provides a view substantially similar to what the person would see without wearing the head-worn unit;
a first image that is not responsive to pitch of the person's head and not responsive to roll of the person's head;
a second image responsive to a pitch signal and a roll signal from the orientation sensing element;
at least one element responsive to a nystagmus signal from the video camera;
a battery; and
power management circuitry further comprising a charging port;
biometric sensors attachable to the person comprising one or more of:
a blood oxygen sensor;
a heart-rate sensor;
an electrocardiogram;
a respiration sensor;
a core body temperature sensor;
a skin temperature sensor;
an inhaled gas level sensor;
an exhaled gas level sensor;
a trunk position sensor; or
a limb movement muscle flex and contraction sensor;
environmental sensors comprising one or more of:
a temperature sensor;
a pressure sensor;
an oxygen sensor;
a light level sensor; or
an engine vibration sensor;
a vehicle, wherein;
the vehicle is responsive to the nystagmus signal originating from the video camera;
communication between the video camera and the vehicle further comprises communication through a dongle;
the vehicle is responsive to at least one of the biometric sensors;
the vehicle is responsive to at least two of the environmental sensors; and
the vehicle comprises:
seats;
a see-through window allowing the person to see a region forward of the vehicle;
vehicle-centric sensors connected to a central processing unit via a sensor interface, the vehicle-centric sensors further comprising:
an attitude sensor;
an altitude sensor;
a heading sensor;
a speed sensor; and
a navigation sensor;
a vehicle display responsive to the speed sensor; and
a vehicle power control input device.

2. The system of claim 1 wherein:
the orientation sensing element further comprises a yaw sensing element wherein the yaw sensing element is responsive to rotation about an third axis orthogonal to the first and second axes and wherein the head attachable display further comprises a third image responsive to the yaw sensing element;

the head-attachable display is responsive to the light level sensor;

the head-attachable display further comprises an arrayed waveguide display;

the first image comprises a maximum of one horizontal line and a maximum of one vertical line;

the second image further comprises a first movable line, a second moveable line and two triangles wherein:

the first movable line is substantially horizontal when the person is upright, the person is facing forward, the person's head is not tilted, and the person is in a stationary environment;

the second moveable line is perpendicular to the first moveable line;

the second moveable line is shorter than the first moveable line;

the second moveable line is located predominantly on one side of the first moveable line; and at least one of the first moveable line, the second vertical line, and the two triangles changes color in response to the orientation of the first image relative to the second image;

at least one of the first moveable line, the second vertical line, and the two triangles is generated digitally using a graphics library;

the location of first image and the second image may be moved from the center of view to a position at least 10 degrees higher than the center of view and at least 30 degrees to either the left or right of the center of view in the head attachable display in response to the nystagmus signal;

the altitude sensor further comprises:

a sea level altitude sensor;

a hard deck altitude sensor; and a density altitude sensor; and the system is used to manage gravitational force induced loss of consciousness.

3. A system comprising a unit attachable to a person's head wherein the head-attachable unit further comprises:

an orientation sensing element responsive to rotation about a first axis representing a rotation selected from the group consisting of:

pitch of the person's head, and roll of the person's head;

an eye sensor comprising a video camera, wherein the video camera is responsive to an ocular movement selected from the group consisting of:

horizontal nystagmus detected as temporal involuntary horizontal eye movement caused by self-perceived motion sensation as a result of a physiological effect including one or more of vertigo, motion sickness, motion intolerance, or spatial disorientation resulting from sensory mismatch between the person's visual, vestibular, and proprioceptive organs;

vertical nystagmus detected as temporal involuntary vertical eye movement caused by self-perceived motion sensation as a result of a physiological effect including one or more of vertigo, motion sickness, motion intolerance, or spatial disorientation resulting from sensory mismatch between the person's visual, vestibular, and proprioceptive organs; and torsional nystagmus detected as temporal involuntary eye rotation caused by self-perceived motion sensation as a result of a physiological effect including one or more of vertigo, motion sickness, motion intolerance, or spatial disorientation resulting from sensory mismatch between the person's visual, vestibular, and proprioceptive organs;

a display viewable by the person wherein the display comprises:

a first image that is not responsive to pitch of the person's head and not responsive to roll of the person's head;

a second image responsive to a rotation signal from the orientation sensing element.

4. The system of claim 3 wherein the display is responsive to a nystagmus signal from the video camera.

5. The system of claim 3 further comprising a communications module wherein the communications module transmits a nystagmus signal to a vehicle.

6. The system of claim 3 wherein the video camera is responsive to:

horizontal nystagmus;

vertical nystagmus; and torsional nystagmus.

7. The system of claim 3 wherein:

the orientation sensing element further comprises:

a circuit board;

interface circuitry;

communications circuitry;

a central processing unit;

a memory unit;

a micro-electro-mechanical system integrated circuit wherein the micro-electro-mechanical system further comprises an accelerometer;

the orientation sensing element is responsive to both pitch and roll of the person's head; and the second image is responsive to both pitch and roll signals from the orientation sensing element.

8. The system of claim 3 wherein the system is used to manage gravitational force induced loss of consciousness.

9. The system of claim 3 wherein the system is used in a sports application.

10. The system of claim 3 wherein the system is used in a medical application.

11. The system of claim 3 wherein the system is used in a gaming application.

12. The system of claim 3 wherein the system is used in a zero gravity application.

13. The system of claim 3 wherein the display comprises a 3-dimensional display.

14. The system of claim 3 wherein the display comprises a technology selected from the group consisting of:

organic light emitting diode technology;

liquid crystal on silicon technology;

wave guide array technology;

low temperature polysilicon technology; and excimer laser annealing display technology.

15. The system of claim 3 wherein the system further comprises a dongle for connecting the system to a vehicle and wherein the dongle further comprises:

an electrical power source;

an electrical charger;

a sensor interface; and an avionics interface.

16. A nystagmus detection method, the method comprising the steps of:

establishing a portable head-attachable unit wherein establishing further comprises a video-camera-based eye sensor, a motion sensor; and a see-through display;

attaching the head-attachable unit to a user's head in a position that allows the user to see the display;

presenting a first symbol on the display that stays in a fixed location when the user's head moves;
presenting a second symbol on the display that is responsive to the motion sensor;
receiving a first head motion signal from the motion sensor at a first time;
receiving a second head motion signal from the motion sensor at a second time;
measuring a first nystagmus intensity at a first time wherein measuring further comprises using the eye sensor to detect user eye motion selected from the group consisting of:
  involuntary horizontal eye movement caused by self-perceived motion sensation as a result of a physiological effect including one or more of vertigo, motion sickness, motion intolerance, or spatial disorientation;
  involuntary vertical eye movement caused by self-perceived motion sensation as a result of a physiological effect including one or more of vertigo, motion sickness, motion intolerance, or spatial disorientation; and
  involuntary eye rotation caused by self-perceived motion sensation as a result of a physiological effect including one or more of vertigo, motion sickness, motion intolerance, or spatial disorientation;
measuring a second nystagmus intensity at a second time;
generating an alarm signal in response to the first head motion signal, the second head motion signal, the first nystagmus signal, and the second nystagmus signal.

17. The nystagmus detection method of claim 15 further comprising the step of altering the information on the display in response to the alarm signal.

18. The nystagmus detection method of claim 15 further comprising the step of communicating the alarm signal to a vehicle.

19. The nystagmus detection method of claim 15 wherein establishing further comprises battery-powered eyeglasses.

20. The nystagmus detection method of claim 16 wherein:
establishing further comprises a first video camera for the right eye and a second video camera for the left eye; and
measuring further comprises measuring nystagmus in the user's left eye and measuring nystagmus in the user's right eye.

* * * * *